United States Patent [19]
Brois et al.

[11] Patent Number: 4,965,375
[45] Date of Patent: Oct. 23, 1990

[54] THIO-BIS-(ALKYL LACTONE ACID ESTERS) AND THIO-BIS-(HYDROCARBYL DIACID ESTERS) ARE USEFUL ADDITIVES FOR LUBRICATING COMPOSITIONS

[75] Inventors: Stanley J. Brois, Westfield; Antonio Gutierrez, Mercerville, both of N.J.

[73] Assignee: Exxon Research and Engineering Co., Florham Park, N.J.

[21] Appl. No.: 401,399

[22] Filed: Aug. 31, 1989

Related U.S. Application Data

[60] Division of Ser. No. 184,627, Apr. 22, 1988, Pat. No. 4,866,187, which is a continuation of Ser. No. 804,306, Dec. 3, 1985, abandoned, which is a division of Ser. No. 528,213, Aug. 31, 1983, Pat. No. 4,568,756, which is a division of Ser. No. 173,299, Jul. 24, 1980, Pat. No. 4,417,062, which is a division of Ser. No. 954,051, Oct. 23, 1978, Pat. No. 4,239,636, which is a continuation-in-part of Ser. No. 768,265, Mar. 14, 1977, Pat. No. 4,123,373, and Ser. No. 806,326, Jun. 13, 1977, Pat. No. 4,167,514, which is a division of Ser. No. 726,206, Sep. 24, 1976, Pat. No. 4,062,786.

[51] Int. Cl.$^5$ ............................................. C07D 407/12
[52] U.S. Cl. .................................................... 549/320
[58] Field of Search ......................................... 549/320

[56] References Cited

U.S. PATENT DOCUMENTS 4,568,756  2/1986  Brois et al. ........................... 549/320

Primary Examiner—Glennon H. Hollrah
Assistant Examiner—Amelia A. Owens
Attorney, Agent, or Firm—Vivienne T. White

[57] ABSTRACT

Thio-bis-(hydrocarbyl substituted diacid materials), such as thio-bis-(polyalkyl lactone acid) and/or their precursors, the adducts of sulfur chloride and unsaturated diacid materials, e.g., 4,8-bis-polyalkyl-4,8-dichloro-6-thiaundecane-1,2,10,11-tetracarboxylic acid bis-anhydride and their dehydrochlorinated analogs, when esterified with an alcohol, preferably a polyol, such as pentaerythritol, polypentaerythritol or a polyalkylene glycol with or without acid catalysts and/or metal template ragents yield thio-bis-(alkyl lactone acid esters) and thio-bis-(hydrocarbyl diacid esters) which can be characterized in part, as macrocyclic and/or macrocyclic-like structures, are useful as stable additive in lubricating compositions, e.g. as varnish inhibiting dispersants for lubricating oils and fuels.

5 Claims, No Drawings

THIO-BIS-(ALKYL LACTONE ACID ESTERS) AND THIO-BIS-(HYDROCARBYL DIACID ESTERS) ARE USEFUL ADDITIVES FOR LUBRICATING COMPOSITIONS

Divisional application of U.S. patent application Ser. No. 184,627, filed Apr. 22, 1988 now U.S. Pat. No. 4,866,187 which is a R. 60 continuation of U.S. Ser. No. 804,306, filed Dec. 3, 1985 now abandoned which is a Rule 60 divisional of U.S. Ser. No. 528,213, filed Aug. 31, 1983, now U.S. Pat. No. 4,568,756 which is a Rule 60 divisional of U.S. Ser. No. 173,299, filed July 24, 1980 (now U.S. Pat. No. 4,417,062), which is a divisional of U.S. Ser. No. 954,051, filed Oct. 23, 1978 (now U.S. Pat. No. 4,239,636), which is a CIP of U.S. Ser. No. 768,265, filed Mar. 14, 1977 (now U.S. Pat. No. 4,123,373) and U.S. Ser. No. 806,326, filed June 13, 1977 (now U.S. Pat. No. 4,167,514) which is a Rule 60 divisional of U.S. Ser. No. 726,206 filed Sept. 24, 1976, (now U.S. Pat. No. 4,062,786).

BACKGROUND OF THE INVENTION AND PRIOR ART

The present invention concerns hydrocarbon soluble thio-bis-(alkyl lactone acid esters) and thio-bis-(hydrocarbyl diacid esters), their method of preparation and their utility, preferably, in hydrocarbon fuel and lubricating systems, as stable sludge dispersants, varnish inhibitors, antioxidants, antiwear agents and lubricity additives.

During the past decade, ashless sludge dispersants have become increasingly important, primarily in improving the performance of lubricants and gasoline, in keeping the engine clean of deposits, and permitting extended crankcase oil drain periods. One category of ashless dispersants involves esters of alkenyl substituted acids, e.g. polyisobutenyl succinic acids, with polyols e.g., pentaerythritol, as taught in U.S. Pat. No. 3,381,022; however, such dispersants oftentimes contain olefinic unsaturation making them susceptible to oxidative degradation especially under high severity conditions such as elevated oil temperatures and extended drain intervals.

A second category involves chloro lactone ester dispersants prepared via the esterification of alkenyl chloro lactone acids with pentaerythritol as taught in U.S. Pat. No. 3,755,173; however, the inherent propensity of such dispersants, or antirust compounds as taught in U.S. Pat. No. 2,279,688 towards elimination of corrosive HCl to give unsaturated products, can promote decomposition of the hydrocarbon lubricant, corrode metal engine parts, and promote varnish deposition on the internal surfaces of the engine.

Thus, the effectiveness of dispersants of either category, particularly at higher temperatures, can be markedly impaired by oxidative degradation. Besides, not only do such systems suffer from instability problems, but the potency of such dispersants oftentimes, owing to inherent limitations in their sludge binding capacity, diminishes with increasing severity of operating conditions. The present invention overcomes the shortcomings of the prior rt by designing novel thio-bis-(polyalkyl lactone acid esters) and thio-bis-(hydrocarbyl diacid esters) with enhanced stability and potency. The stabilization of these novel dispersant systems may be ascribable to the lack of unsaturation and/or the presence of sulfide functionality which endow these systems with enhanced stability and antioxidant properties. The enhanced potency may be related, in part, to the macrocyclic and/or macrocyclic-like configuration assumed by the polar sulfur and oxygen (heteroatom) functionality in some of the dispersant molecules. Such circular-like arrangements of ligands endow these novel systems with remarkable binding and/or chelation properties and in some instances, inclusion properties, making these dispersant systems uniquely effective even under high severity conditions.

We propose herein, novel and improved dispersant systems based on host-guest chemistry wherein the polar head of the host molecule (dispersant) assumes or is capable of assuming a macrocyclic-like configuration so that the resulting circular-like array of heteroatoms (e.g. sulfur, oxygen and nitrogen), on the polar head effectively binds guest ions and molecules, including metals and sludge components, within the cyclic-like structure, or between host molecules to form s sandwich-like structure with guest molecules in the middle.

SUMMARY OF THE INVENTION

It has now been discovered that hydrocarbon-substituted thioethers, which feature, in part, vicinal lactone and ester functions, can be arranged in a macrocyclic-like configuration using novel synthetic methods whereby a highly stable additive of enhanced dispersancy, enhanced viscosity properties, and antioxidant properties can be realized. This novel class of macrocyclic-like additive can be represented, in part, as an ester of 6,6'-thio-bis-(4,5,6-trisubstituted-3,5-carbolactone-hexanoic acid) as featured by the formula:

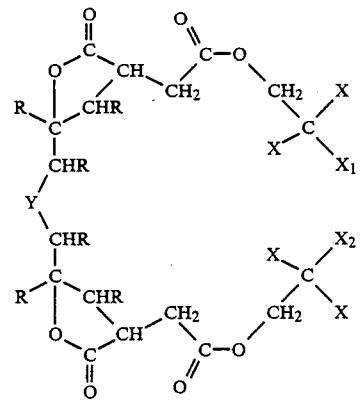

wherein R is selected from the group consisting of hydrogen, hydrocarbyl and substituted hydrocarbyl containing from 1 to 10,000, preferably 12 to 200, carbons with the restriction that at least one R has at least about 4 carbons; the bridging or coupling element, Y, is selected from the group consisting of S (thio), S—S (dithio), S=O (sulfinyl), $SO_2$ (sulfonyl), Se (seleno), S—$(CH_2)_z$S— where z is a number of from 2 to 10, X, $X_1$ and $X_2$ are selected from the group consisting of hydrogen, alkyl, hydroxyl, acyloxy, hydroxyalkyl, $CH_2OCH_2C(CH_2OH)_3$, and —$O(CH_2$—$CH_2O)_nH$ where n is 1 to 50 and preferably at least one X group contains a hydroxy moiety, and that typically $X_1$ and $X_2$ are hydrogen bonded so as to form a macrocyclic-like configuration. In some cases, depending on stoichiometry, the nature of the reactants, and the mode of synthesis, $X_1$ and $X_2$ together can represent a linking group such as O, S, S—S, N-alkyl, —$CH_2OCH_2$, —CH- $_2OCH_2$—$C(CH_2OH)_2$—$CH_2OCH_2$—, —$O(CH_2CH_2O)_n$—, wherein n is 1–50; such linking groups create equimolar [(i.e., one mole of thio bis-(acylating agent) to one mole of polyol (1:1)] macrocyclic ring structures of varying sizes and composition depending upon the nature of the thio-bis-(acylating reagent) and the polyhydric alcohol. Sometimes, $X_1$ and $X_2$ may bond to another molecule of thio-bis-(acylating agent) e.g. thio-bis-(lactone acid) in which instance, two acylating reactants essentially combine with two polyols (2:2) to yield structurally larger macrocyclic esters of doubled molecular weight. Furthermore, equimolar ester products of thio-bis-(acylating agent) and polyol are capable of forming, under suitable reaction conditions, ever larger macrocyclic structures, e.g. (3:3), (4:4), etc. Usually, mixtures of linear and cyclic ester oligomers are formed, and the ratio of cyclic to linear oligomers is a sensitive function of reaction conditions, and the nature of the reactants; however, with a judicious choice of experimental conditions, one can achieve a suitable mix of cyclic and linear esters for specific end uses.

It is noteworthy that the presence of a metal ion such as lithium, sodium, potassium, copper, zinc, nickel and cobalt, or alcoholate of such metals as titanium, tin and silicon, in catalytic or stoichiometric amounts during esterification or bridging, tends to increase the yield of macrocycles over the products of competing linear polymerizations, a phenomenon known as the template effect. In such cases, the formation of macrocycles are presumably mediated via the template action of these metals. Obviously, such metal ion assisted cyclizations provide a variety of useful cyclic ligands and their complexes for additive applications. In such cases, the metal ion or alkoxide species, depending upon its effective size, forms a template about which the polyol and thio-bis-(acylating agent) can react to form 1:1, 2:2, and 3:3 and larger macrocycles in substantial yields. The ability to control the mode of esterification with certain ions and acidic solid phase systems provides a convenient and novel approach to tailoring the composition of an ester product to meet specific viscosity and performance requirements.

Preferred herein are mono- and dithio-bis-(alkyl lactone polyol esters and simple esters) of number average molecular weight (Mn) ranging from about 400 to about 140,000 prepared by the reaction of a thio-bis-(alkyl lactone carboxylic acid) or its precursor, a $S_xCl_2$-olefin diacid adduct wherein x is 1 or 2, with a simple alcohol such as methanol or a polyol at about 20°–240° C. or preferably 50°–200° C. until the esterification and lactonization (where operative) events are complete by IR analysis. To achieve substantial lactone formation in the esterification of $S_xCl_2$-olefin diacid adducts with polyols, the use of soluble acids, or resin acids, or acidic solid phases such as silica gel, is essential.

These novel compounds described above are effective as dispersants, inhibitors, antiwear and/or lubricity additives which are particularly useful in lubricating oil compositions and are also useful as additives in distillate fuel compositions and gasoline as well as synthetic lubricating oils and automatic transmission fluids. Thus, it is within the scope of this invention to dissolve a small but at least an effective amount of said compounds of the invention in a major proportion of a hydrocarbon material to provide useful hydrocarbon compositions.

These preferred hydrocarbon soluble compounds have at least 4 carbons in the substantially saturated aliphatic hydrocarbyl groups with preferably one carboxylic acid group of each terminal dicarboxylic acid function converted into a lactone ring and the other carboxylic acid group converted into a polyol ester as a result of the reaction of at least an equivalent amount of said thio-bis-(hydrocarbyl substituted diacid material), including both the diacid and anhydride, and a molar amount of a polyol or polyalkylene glycol, having about 2 to 20 hydroxy groups and containing a total of 2 to 100 carbons.

The novel thio-bis-(alkyl lactone acid esters) of the present invention can be prepared by heating together thio-bis-(alkyl lactone acids or esters), or $YCl_2$-polyalkene diacid or anhydride adducts (Y having the meaning previously given) with 1–2 moles of polyol via the conventional method or by a template procedure. The latter option involves esterification in the presence of a metal ion or alcoholate which presumably induces the reaction of condensing functional groups within its coordination sphere (template effect) so as to generate macrocyclic esters in the equimolar reaction of thio-bis-(acylating agents) and polyols.

The conventional method involves the esterification of thio-bis-(alkyl lactone acid) and/or its precursor, the $S_xCl_2$-olefin diacid adduct with 1–2 moles of polyol, preferably in the presence of an acid catalyst, and is featured in the equation:

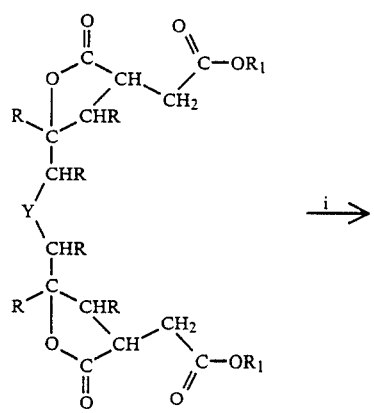

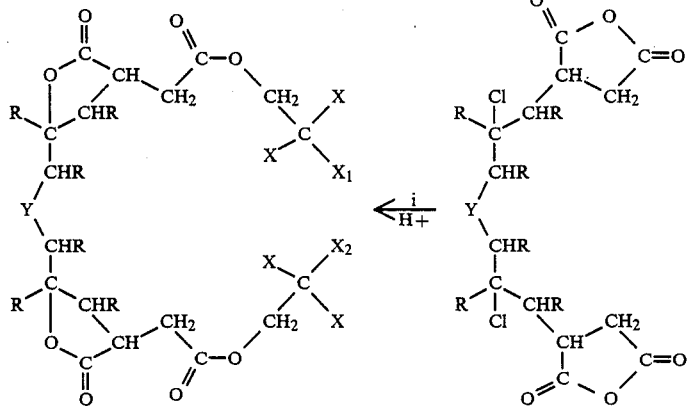

wherein: R, Y, $X_1$ and $X_2$ are as earlier defined in the formula representing, in part, the novel class of macrocyclic-like additive; $R_1$ is hydrogen or an alkyl group containing from 1 to 5 carbons; H+ represents an acid catalyst; and, i refers to a polyol reactant which can be represented by the formula

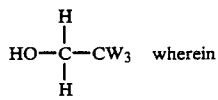

W can be X, $X_1$ or $X_2$.

The adduct depicted in the above equation is readily converted to the acid or simple ester by hydrolysis with water or esterification with a $C_1$ to $C_5$ monohydric alcohol.

It has been further discovered that other useful thio-bis-(acylating agents) comprising (i) thio-bis-(alkenyl diacid/anhydride/ester) prepared via chlorosulfenylation of olefin diacids with sulfur halides, at higher reaction temperatures, and (ii) dithio-bis-(alkyl diacid/anhydride/ester) prepared by means of sulfur bridging with thiols under oxidative conditions, when subsequently esterified with a polyol afford novel additives possessing lubricating oil dispersancy, lubricity modification and/or friction modification properties.

DETAILED DESCRIPTION OF THE INVENTION

In the following description of this invention, the reactants, i.e., thio-bis-acylating agents, their formation via the bridging (or coupling) of alkene diacid materials with a sulfur halide or a sulfur halide equivalent such as a sulfenate ester-HCl combination reagent or a thiol-halogen combination reagent; the esterification reactions of the bridged acylating agents with polyols in the presence of acids and metal templating reagents, and utilization of the novel ester products are set forth below in detail.

THIO-BIS-(ACYLATING REAGENTS)

The preparation of the mono- or dithio-bis-(lactone alkanoic acid or ester), mono- or dithio-bis-(alkene dioic acid or anhydride or ester) or dithio-bis-(alkane dioic acid or anhydride or ester) acylating agents involve the sulfur halide coupling or bis-sulfenyl halide-induced coupling or the oxidative coupling of $H_2S$ or thioacid adducts of an olefin diacid. The olefin diacid is readily obtained via the reaction of an olefin or a chlorinated olefin with an unsaturated $C_4$ to $C_{10}$ dicarboxylic acid, anhydride or ester thereof, such as fumaric acid, itaconic acid, maleic acid, maleic anhydride, dimethyl fumarate, etc. The dicarboxylic acid material formed via the Ene reaction of an olefin with maleic anhydride can be illustrated as an alkenyl-substituted anhydride which may contain a single alkenyl radical or a mixture of alkenyl radicals variously bonded to the cyclic succinic anhydride group, and is understood to comprise such structures as:

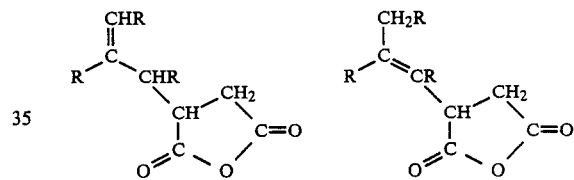

with the γ, δ-unsaturated isomers predominating and wherein R may be hydrogen or hydrocarbyl or substituted hydrocarbyl containing from 1 to about 10,000 and more carbons with the restriction that at least one R has at least 1 carbon, preferably from about 16 to about 400 carbons and optimally from about 60 to about 100 carbons. The anhydrides can be obtained by well-known methods, such as the reaction between an olefin and maleic anhydride or halosuccinic anhyhdride or succinic ester (U.S. Pat. No. 2,568,876). In branched olefins, particularly branched polyolefins, R may be hydrogen, methyl or a long chain hydrocarbyl group. However, the exact structure may not always be ascertained and the various R groups cannot always be precisely defined in the Ene products from polyolefins and maleic anhydride.

Suitable olefins include butene, isobutene, pentene, decene, dodecene, tetradecene, hexadecene, octadecene, eicosene, and polymers of propylene, butene, isobutene, pentene, decene and the like, and halogen-containing olefins. The olefins may also contain cycloalkyl and aromatic groups. The most preferred alkenyl succinic anhydrides used in this invention are those in which the alkenyl group contains a total of from 4 to 400 carbon atoms; and, at least 16 to 400 and more preferably 60 to 100 for mineral oil systems.

Many of these hydrocarbyl substituted dicarboxylic acid materials and their preparation are well known in the art as well as being commercially available, e.g. 2-octadecenyl succinic anhydride and polyisobutenyl succinic anhydride.

With 2-chloromaleic anhydride and related acylating agents, alkenylmaleic anhydride reactants are formed. Bridging of these products with YCl₂ also afford useful precursors to thio-bis-(lactone ester) products.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other copolymers include those in which a minor molar amount of the copolymer monomers, e.g., 1 to 20 mole % is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have number average molecular weights ($M_n$) within the range of 500 and about 140,000; more usually between about 700 and about 10,000. Particularly useful olefin polymers have ($M_n$) within the range of about 700 and about 5,000 with approximately one terminal double bond per polymer chain. An especially valuable starting material for a highly potent dispersant additive are polyalkenes e.g. polypropylene and polyisobutylene, having about 90 carbons.

The dicarboxylic acid materials (Diels-Alder adducts) formed via the reaction of a chlorinated olefin with maleic anhydride also useful in the present invention, can be illustrated in part, by the following structures:

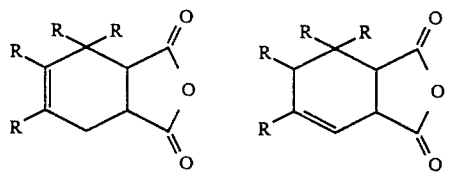

where R is as previously defined. Useful chlorinated olefins include chlorinated di-isobutylene, tri-isobutylene, polyisobutylene, tetrapropylene, polyisopropylene, and alkenes which upon halogenation characteristically afford allylic halide structures.

Hemi-ester or diacid reactants can be constructed readily from the anhydride products obtained via the Ene process by the scission of the anhydride ring with a mole of alcohol or water. Normally, the ring opening process is effected by interacting equimolar amounts of anhydride and alcohol or water at temperatures of 25° C. to about 120° C. without diluent or with a suitable solvent such as tetrahydrofuran, p-dioxane, 1,2-dimethoxy-ethane, etc. In conversions to the diacid, excess water may be added to accelerate the ring scission process. With alcohols, excess alcohol may lead to some di-ester formation, and accordingly equimolar reaction stoichiometry, is preferable. In the absence of strong acid catalysts, however, excess alcohol can be used to effect hemi-ester formation. Suitable alcohol reactants include methanol, ethanol, isopropanol, butanol or other simple monohydric alcohols which can be removed readily by evaporation or distillation.

BRIDGING REACTIONS

The bridging or coupling of the precursor acylating agents can be achieved via a choice of synthetic options including (i) addition of sulfur halides or bis-sulfenyl halides or alkyl sulfenate/HCl reagent to unsaturated diacids, hemi-esters, diesters or anhydrides, (ii) the oxidative coupling of unsaturated acids previously thiylated with $H_2S$ or $R_1C(=O)SH$, where $R_1$ represents a $C_1-C_5$ alkyl group, or (iii) reaction of α,ω-alkanedithiols, $H_2S$, or a suitable thiylating agent, with epoxidized or halogenated alkene dioic acid or anhydride materials. Synthetic approaches (i) and (ii) are described in detail herein.

In contrast to the facile and effective modes of sulfur bridging outlined above, other possible synthetic options including the sulfurization of olefin diacid materials with elemental sulfur, and the Ene reaction of alkenyl sulfides do not provide discernable amounts of stable, sulfur-bridged olefin diacid materials.

The prior art clearly teaches that the sulfurization of alkenes with elemental sulfur gives complex mixtures of unsaturated, unstable polysulfides and polymeric sulfides up to about 140° C., and at higher temperatures, ca. 170° C., the polysulfidic products owing to limited thermal stability, undergo extensive decomposition to yield hydrogen sulfide, thiols, 1,2-dithiole-3-thiones and/or thiophenes as the major products. These results are in complete harmony with published reports which elaborate upon the chemistry of sulfurized olefins: (See L. Bateman and C. G. Moore, "Organic Sulfur Compounds", edited by N. Karasch, Pergamon Press, New York, 1961, Vol. I., pages 210–228). Moreover, sulfurization of alkenylsuccinic anhydrides with elemental sulfur also generates thioanhydride products which tend to eliminate hydrogen sulfide when treated with protic reagents such as polyols.

Finally, the Ene reaction of disulfides with maleic anhydride does not engender the desired Ene product, but affords only low yields of 2-alkylthiasuccinic acid derivatives in a neither clean nor synthetically attractive reaction. This observation is totally consistent with the prior art (See L. Field, "Journal of Organic Chemistry", Vol. 39, No. 14, p. 2110–2112 (1974)).

BRIDGING WITH SULFUR HALIDES

The preferred pathway to bridged acylating agents involves the reaction of sulfur halides, bis-sulfenyl halides or a sulfenate ester-HCl reagent with unsaturated diacids, hemi-esters, di-esters or anhydrides in the temperature range of −60° C. to about 100° C., optimally from about 10° C. to 50° C. If desired, solvents comprising hydrocarbons such as pentane, hexane, heptane, cyclohexane, mineral oil; halocarbons such as methylene chloride, chloroform, carbon tetrachloride, aromatics such as toluene, chlorobenzenes, xylene; ethers, such as diethyl ether and tetrahydrofuran (THF); and, acids such as acetic, propionic and trifluoroacetic acid, can be used in favorably controlling viscosity and reaction temperature. The mode of addition of reagents is dictated by convenience. Usually, the sulfur halide is added dropwise to an unsaturated diacid, ester, or acid anhydride, preferably diluted in an inert diluent. With reactive diluents, namely those containing unsaturates including aromatics, and olefins such as polyisobutylene, sufficient sulfur halide must be added to effect complete bridging of the olefin diacid reactants.

When the addition of one mole of sulfenyl halide to 2 moles of alkene dioic acid anhydride is conducted at low temperatures, e.g. −60° C. to about 20° C., a discrete YCl₂-anhydride adduct forms via the intermediacy of the 1:1 addition product as depicted in the equation:

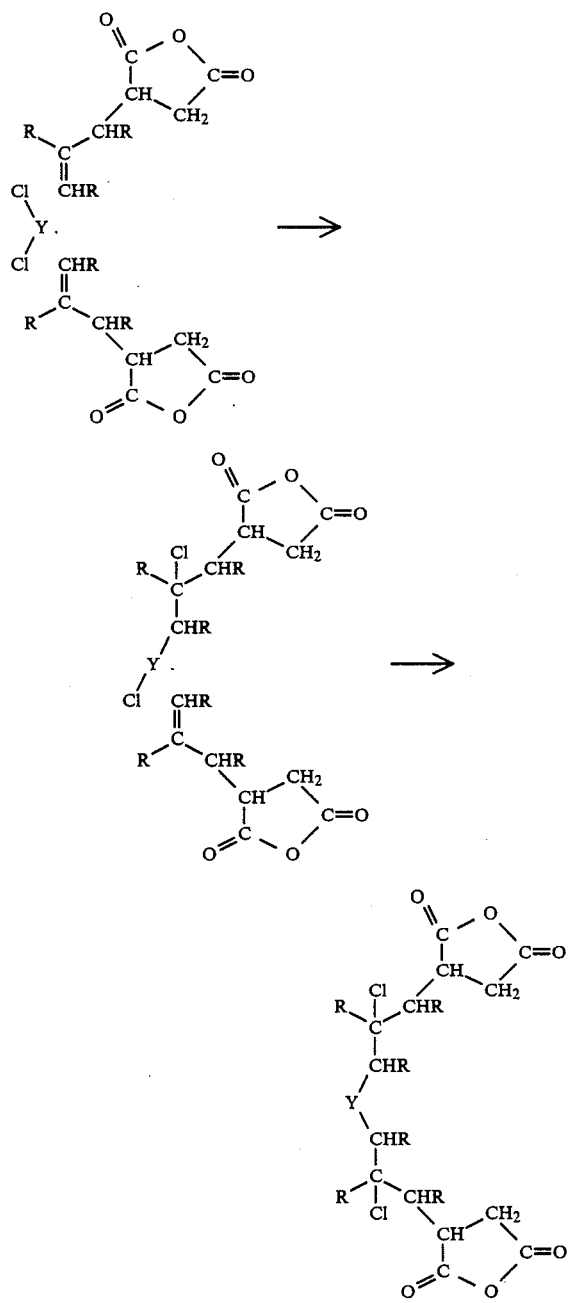

with R and Y being the same as previously defined. The anhydride reactants can be the same or different so that mixtures of symmetrical and unsymmetrical bridged anhydride products can be constructed at will. Higher conversions to unsymmetrical adducts can be achieved by the interaction of equimolar amounts of $YCl_2$ and one type of alkene dioic acid or anhydride at low temperatures to generate a 1:1 adduct. Subsequent addition of a second type of unsaturated anhydride affords the unsymmetrical bridged acylating agent predominantly.

In some cases, it may be convenient to carry out bridging using an alkyl sulfenate ester since such esters are readily converted to sulfur halides upon treatment with a hydrohalide acid under mild conditions, e.g. 0°–20° C. in the presence of an alkene diacid. Alkyl sulfenate esters, such as di-isopropoxy sulfide and/or disulfide are highly versatile, stable precursors to sulfur halides and accordingly, can be combined with an olefin diacid reactant in the proper molar ratio (1:2) and effectively bridge the diacid reagent via the in situ conversion of the sulfenate ester into sulfur halide by the gradual addition of gaseous HCl. Substantial yields of sulfur-bridged acylating agents can be realized via this novel route.

Increasing bridging temperature above about 50° C., and branching in the hydrocarbyl portion of the alkene dioic anhydride tend to accelerate the elimination of HCl from the $YCl_2$-alkene dioic anhydride adduct. Since unsaturated bridged products can be further sulfenylated with $YCl_2$ reagent (re-addition), it becomes necessary in some cases, to modify the theoretical 2:1 stoichiometry to effect complete bridging. Accordingly, at higher temperatures, i.e. from 50°–100° C., ratios in the range of 1.5:1 to 1:1 may be required to realize higher conversions to bridged structures due to re-addition reactions, and the partial thermal decomposition of the sulfur halide reactant at elevated temperatures. While more sulfur halide reagent becomes necessary to achieve coupling, the additional sulfur incorporated into the dispersant precursor (and occasionally the diluent) tends to endow the resulting thio-ether products with enhanced oxidative stability.

When bridging in accord with the theoretical stoichiometry becomes desirable, high purity chlorosulfenylating reagent (distilled $SCl_2$), lower sulfenylating temperatures, and select thio-(bis-acylating reagents) comprising hemi-ester, and/or diacid reactants, dissolved in a minimal amount of olefinic diluent, provide useful synthetic options in realizing more efficient coupling processes. The concept of bridging hemi-ester and/or diacid reactants which tend to be more amenable to lactonization is depicted in the equation:

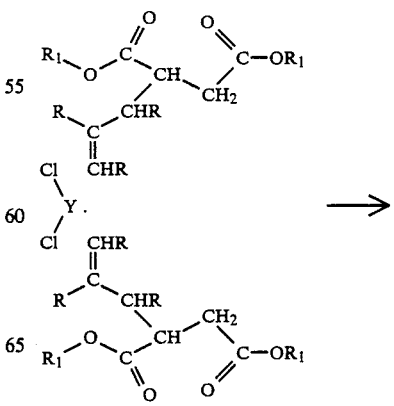

-continued

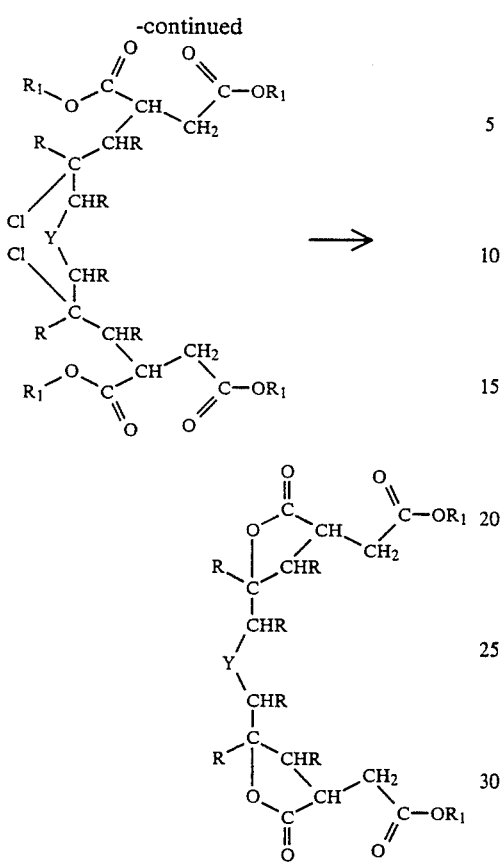

wherein R and $R_1$ are the same as earlier defined. The $YCl_2$ addition to the alkenyl hemi-ester, diester or di-acid previously freed of olefinic diluents by silica gel extraction, affords discrete adducts which can be lactonized via a temperature-sensitive, internal displacement of chloride by a vicinal carboxylic acid or ester group. Chloride displacement with resultant lactonization circumvents the elimination of HCl which would otherwise lead to thio-bis-(alkene dioic acid or esters) products.

It should be noted, however, that treatment of the latter sulfur-bridged unsaturated acylating agent with polyol to effect its esterification usually generates mixtures of thio-bis (lactone acid ester) and thio-bis (alkene diacid ester); however, selective conversions to thio-bis (lactone acid ester) can be achieved prior to or during esterification, by using acid catalysts comprising soluble acids such as sulfuric acid, alkyl sulfonic acids (where alkyl corresponds to a $C_1$ to $C_{60}$ aliphatic radical selected from the group consisting of open chain alkyl, isoalkyl, and cycloalkyl); alkyl aromatic sulfonic acids (where alkyl is defined as above and the aromatic groups can be derived from benzene, toluene, xylene, mesitylene and naphthalene); suitable alkyl aromatic sulfonic acids include i-dodecyl benzene sulfonic acid (Petrostep A-60, Stephan Chemical Co.), i-dodecyl benzene sulfonic acid (Ultrawet 99LS from Arco Chemical Co.) and i-tetracosyl benzene sulfonic acid (SA 119, Esso Chimie, France); Lewis acids such as $BF_3$, $BF_3$ etherate, $AlCl_3$; and resin acids including resin sulfonic acids such as Amberlyst 15 (Rohm and Haas Company, Philadelphia, Pa.) and perfluorinated resin sulfonic acids such as NAFION-H (E.I. DuPont de Nemours and Co., Inc. Wilmington, Del. are suppliers of NAFION perfluorosulfonic acid products); and finally, acidic solid phase catalysts, including silica gel (activated, Grade H, mesh size 100-200 from Davison Chemical, Baltimore, Md.), alumina (acid $Al_2O_3$) silica alumina, zeolite, and certain clays. Silica gel-induced lactonizations are highly useful, since it is believed that the silica gel plays a dual role as a lactonization catalyst and as a template for generating in part, macrocyclic-like products.

As indicated above, sulfur halides including $SCl_2$, $S_2Cl_2$ and alkyl sulfenate ester/HCl reagent are suitable bridging agents. Bis-sulfenyl halides derived from alkane, heteroalkane, aromatic, heteroaromatic, and heterocyclic radicals such as

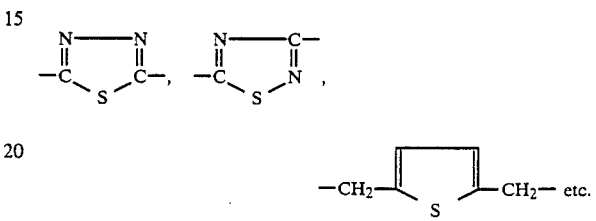

are also useful coupling agents.

Oxidation of the mono-thio ether products (both intermediates and polyol esters) provides access to useful sulfoxide and sulfone derivatives. A variety of inorganic and organic oxidizing agents can be used to effect these conversions including hydrogen peroxide, peracids, hydroperoxides, e.g. t-butyl hydroperoxide, chlorine, positive halogen reagents, nitric acid, oxides of nitrogen, oxygen, ozone and metal oxides. The preferred oxidant is hydrogen peroxide usually in acetic acid and as necessary in an aromatic solvent, e.g. toluene. Oxidation with equimolar quantities of reactants at about 0° to 60° C. provides the sulfoxide in excellent yield. A 2:1 molar ratio of peroxide to said thio ether product produces the sulfone derivative. The peroxide oxidation of sulfides to sulfones is preferably carried out in the presence of catalytic amounts of conventional oxidation catalysts such as tungsten, molybdenum, e.g. molybdenyl acetylacetonate, or vanadium salts.

MECHANISM OF BRIDGING WITH SULFUR HALIDES

The key feature of the addition reactions of sulfur halides, preferably sulfur chlorides or bis-sulfenyl chlorides is their intrinsic ability to couple or bridge a wide variety of unsaturated acid materials in a well-defined manner; this key feature clearly distinguishes the behavior of sulfur halides from other sulfur donors such as elemental sulfur which produces only complex, unstable and ill-defined mixtures of sulfurized products. As indicated above, the sulfur halides add selectively to the point of unsaturation, with a 1:1 sulfenyl chloride adduct being formed initially, followed by the addition of the latter to another unsaturated acid to form a dichloro sulfide adduct as shown in the above equation.

The composition of the adduct hinges on (a) the position of the double bond in said olefin diacid material, and (b) the mode of sulfur halide addition, i.e. an electrophilic addition, as determined by steric and electronic factors. In such electrophilic additions, it is assumed that an episulfonium ion intermediate is formed, although contributions from open ions have not been discounted. Scission of the intermediary episulfonium ion by halide ion from the sulfur halide yields mainly the dihalosulfide isomer depicted in the above equations. The presence of other isomers, however, cannot be precluded. Of greater significance in the assignment of structure to the products of the present invention is the nature of the lactones formed upon hydrolysis or alcoholysis of the adduct The lactonization process seems to involve a carboxyl function either by displacing chlorine from the dichlorosulfide, ring-opening of an intermediary episulfonium ion or adding (via acid catalysis) the carboxy function to an unsaturated site in the adduct.

Judging from the structure of the unsaturated acid reactants from spectral evidence, it is believed that the thio-bis-(lactone acid or ester) products are best illustrated by the structures featuring 5-membered lactone rings as proposed in the above equations. The formation of some six-membered lactones (and even larger ring lactones), however, has been observed by IR spectral analysis, particularly during the polyol or water-induced lactonization of $S_xCl_2$-olefin diacid adducts. Accordingly, 6-ring (or larger ring) lactones and other positional isomers based on the position of sulfur in the bridged structures can also be present in the products of this invention.

BRIDGING WITH THIOLS

In another embodiment of the present invention, thio-bis-(acylating agents) can be constructed via the (i) peroxide or (ii) acid-induced addition of $H_2S$ and/or thioacids to olefin diacid materials to give thiolactone acids and/or thiol-substituted diacids which are then amenable to bridging via (a) oxidative coupling with $Cl_2$, $SO_2Cl_2$, $H_2O_2$, or peracids or (b) displacement reactions with $\alpha,\omega$-alkylene dihalides, e.g. ethylene dichloride.

Alkene dioic acid materials (diacid anhydride or ester) can be readily reacted with $H_2S$ and thioacids under both heterolytic (acid-induced) and homolytic (radical-induced) conditions. Typically, the acid catalyzed reaction affords a product wherein sulfur becomes bonded to the most substituted carbon atom, as shown by the equation:

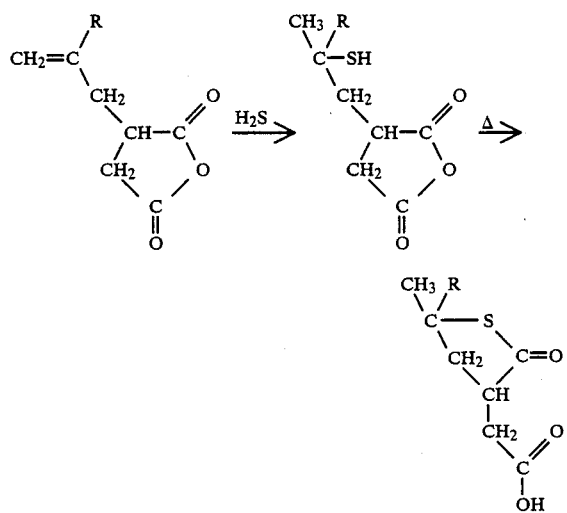

wherein R is as previously defined.

Hydrogen sulfide (usually added in about a two to ten fold excess) reacts with olefin diacid materials (here the anhydride) according to the above equation at comparatively low temperatures, e.g. from about −70° C. to about 25° C. in the presence of ca. 0.1 to about 10 wt. % of such acid catalysts as HCl, $BF_3$, or a chloride salt of Al, Zn, B, P, Sn, Ti and Sn. The aforesaid hydrogen sulfide addition can also be catalyzed with etherates, alcoholates or hydrates of $BF_3$. The $H_2S$ addition products can be isolated as the corresponding thiolactone derivatives owing to the facile lactonization of the mercapto derivative as shown in the above equation. Both the mercapto and thiolactone derivatives can be readily bridged via oxidative coupling or displacement reactions in protic solvents such as water and alcohols.

A synthesis of isomeric thiol-substituted diacid material can also be effected via the homolytic reaction of olefin diacid material with thiols and thioacids. Reactive thiols such as thioacetic acid add readily to the least substituted olefinic carbon atom in alkene dioic acid reagents in the presence of small amounts, e.g. about 0.05 to 1 wt. % of peroxides such as benzoyl peroxide, di-tert-butyl peroxide, to give a thioacyl substituted alkane dioic acid material, which is thereafter oxidized with sulfuryl chloride in methanol to the corresponding symmetrical disulfide product as shown in the equation:

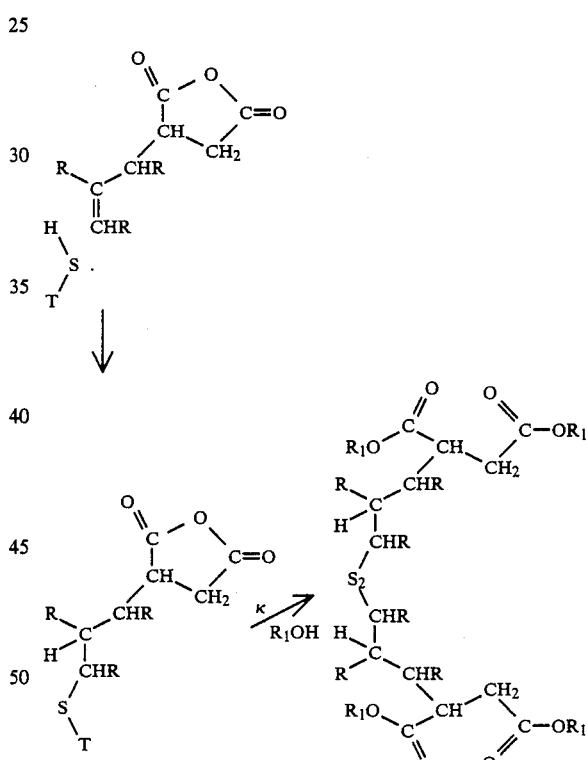

wherein T is a $C_1$ to $C_5$ acyl group, e.g. acetyl; $\kappa$ refers to such oxidants as $Cl_2$, $SO_2Cl_2$, and $H_2O_2$; and R and $R_1$ are the same as previously described.

As seen above, thiolactones and thiol-substituted diacid materials can be easily bridged via oxidative solvolysis using a combination of an oxidant such as air, $H_2O_2$, peroxide, chlorine or $SO_2Cl_2$, and a protic solvent such as water, or alcohol. An alternate preparative option to bridging involves a nucleophilic displacement of the thiol-substituted diacid reagent with $\alpha, \omega$-alkane dihalides including $Cl(CH_2)_nCl$, $Cl(CH_2CH_2S)_nCH_2CH_2Cl$ and $Cl(CH_2CH_2O)_nCH_2CH_2Cl$, wherein n is a number from 1 to 10, and and bis-chloromethylate aromatics, heteroaromatics and heterocycles.

ALCOHOL REACTANTS

1. Monohydric alcohols

Useful monohydric alcohols can be characterized by the formula R'OH wherein R' is an alkyl or heteroalkyl group containing from 1 to 24, preferably 1 to 12, carbons such as methyl, ethyl, propyl, butyl, hexyl, octyl, decyl, lauryl, stearyl and mixtures thereof; and heteroatom-containing aliphatic radicals such as $CH_3O(CH_2CH_2O)_nCH_2CH_2—$, $CH_3S(CH_2CH_2S)_nCH_2CH_2—$, $(CH_3)_2N(CH_2CH_2NCH_3)_nCH_2CH_2—$; etc., where n=1–10, and 1-aza-3,7-dioxabicyclo(3.3.0)oct-5-yl-methanol. The resulting esters when used as additive components for mineral lubricating oils and fuels provide improved properties of antiwear, anticorrosion, friction modification or lubricity modification.

2. Polyhydric alcohols

The polyhydric alcohols used in esterifying the thio-bis-(acylating reagents) can have a total of 2 to about 100 carbon atoms and can be represented by the formula:

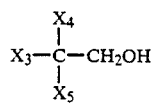

wherein: $X_3$ is hydrogen, $C_1$ to $C_5$ alkyl, hydroxyalkyl; hydroxyalkyl $HO(CH_2)_n$ wherein n is 1–10, hydroxyalkoxy; $HO(CH_2CH_2O)_n—$, wherein n is 1–40, hydroxyalkylthio; $HOCH_2CH_2S(CH_2CH_2S)_n—$, wherein n is 1 to 10; and hydroxyalkylamino; $HO(CH_2CH_2NCH_3)_n—$, wherein n is 1 to 10; and $X_4$ and $X_5$ may be the same or different and represent hydrogen, $C_1$ to $C_5$ alkyl and $C_1$ to $C_5$ hydroxyalkyl groups and their ester, ether, acetal or ketal derivatives. Examples of useful acetals and ketals include mono and bis-formals of pentaerythritol; mono and bis-acetal and benzal analogs of pentaerythritol; and the cyclic formal and acetal of $HO(CH_2CH_2O)_nH$ wherein n is 4–8.

With glycol and polyethylene glycol reactants, esterification of sulfur-bridged acylating reagents preferably in the presence of template reagents, affords in part, simple macrocycles and macrocyclic-like structures (depending on reactant ratios), while reaction of polyols wherein $X_4$ and/or $X_5$ represent hydroxyalkyl substitutents, affords in part, macrocycles and macrocyclic-like species with cage-like configurations capable of entrapping ionic or charged species and thereby providing unique dispersant activity.

An especially preferred class of polyhydric alcohols for designing novel, cage macrocyclic and macrocyclic-like ester products are typified by pentaerythritol, dipentaerythritol, tripentaerythritol, polypentaerythritols, sorbitol, mannitol, cyclohexaamylose, cycloheptaamylose and related polyhydric alcohols such as these prepared via the aldol condensation of formaldehyde with ketones such as acetone, and cyclohexanone, e.g. 2,2,6,6-tetramethylol-1-cyclohexanol. In some instances, enhancement of the above-described caging effect may be carried out by partially esterifying one or both the geminal hydroxyalkyl groups represented by $X_4$ and $X_5$ of the polyol with a carboxylic acid having from about 2 to 18 carbon chain which contains such heteroatoms as nitrogen, sulfur and oxygen.

ESTERIFICATION PROCESS

The thio-bis-(lactone acid esters) and thio-bis-(hydrocarbyl diacid esters) of the present invention can be prepared via (a) a conventional ester synthesis or (b) a template procedure involving ester formation in the presence of a metal salt, or alcoholate.

Using the conventional approach, we contemplate within the scope of the present invention the formation of esters from (i) the $S_xCl_2$-olefin diacid anhydride adduct and its HCl-free analogs via scission of the anhydride ring with polyol in the presence of an acid catalyst, or (ii) the esterification of the thio-bis-(alkyl lactone acid) materials with polyol alone or in the presence of an acid catalyst. The scission of the anhydride ring in option (i) affords a transient hemi-ester species via attack of the polyol at the least congested carbonyl site in the adduct. The incipient carboxyl group of certain hemi-ester intermediates may rapidly displace chloride ion in an intramolecular process to afford a 5-, 6- or larger membered lactone ring. The size of such lactone rings will depend on the position of the chlorine in the adduct, and the specific carboxy group involved in the intramolecular displacement. When elimination of chloride in the $S_xCl_2$-olefin diacid anhydride reactant occurs prior to hemiester formation, which is an event favored at temperatures above about 50° C. especially in $S_xCl_2$-branched olefin diacid adducts, the free carboxy group is either further esterified to provide a thio-bis-(alkene dioate ester) product or adds to the point of unsaturation within the adduct to form 5-, 6- and/or larger membered lactone rings, depending on the position of the double bond. The preferred lactonization process is aided by the presence of the acid catalysts described previously. Typically, the esterification method is carried out by adding about one mole of alcohol, preferably polyol, per 0.5 to 1 mole of thio-bis-(lactone acid or ester or $S_xCl_2$-alkene diacid adduct or it HCl-free analog, with or without an inert diluent, in the presence of sn esterification catalyst, and heating the mixture at 20°–240° C., preferably 50°–220° C. until reaction is complete by infrared analysis of the product as indicated by maximal absorptions for ester and lactone functionality.

Variations, however, in the molecular weight and composition of the sulfur-bridged acylating agent, as well as the molecular weight and polyhydric character of the polyol may be necessary, depending upon utility, since these factors sensitively affect the hydrophilic-lipophilic balance, solubility and the viscosity of the additive.

For example, it has been found that lactone esters obtained from the reaction of one mole of bis-thio-(alkyl lactone acid) or its $S_xCl_2$-olefin diacid adduct precursor (derived from polyisobutenyl succinic anhydride with $M_n \approx 1050$ and a Saponification number of 78) with two moles of pentaerythritol feature outstanding dispersant properties. Moreover, with higher polyhydric alcohols, for example, esters obtained via reaction of equimolar amounts of the above thio-bis-(acylating) agents and tripentaerythritol also featured outstanding dispersant activity.

The superior stability and dispersant properties exhibited by the sulfur-bridged lactone esters and sulfur-bridged hydrocarbyl esters of the present invention over the prior art compositions, namely esters of polyisobutenyl succinic anhydride and polyols such as pentaerythritol, may be related in part, to the presence of sulfide functionality and in part, to the macrocyclic and macrocyclic-like configurations assumed by the polar heteroatoms in some of the dispersant molecules.

METAL ASSISTED CYCLIZATIONS

Although a wide spectrum of macrocyclic-like esters can be constructed via the conventional approach, the template procedure offers a selective synthetic route to macrocycles and their complexes as well in the equimolar reaction of polyol and thio-bis-(acylating agent). In the metal ion assisted process, the cation presumably enhances yields of macrocycles by forming a template about which the sulfur-bridged acylating agent and polyol molecules condense into a macrocyclic species. It is believed that complex formation in the hemiester intermediate accelerates the intramolecular ester formation relative to the intermolecular process which affords polymer product. Factors such as metal ion size, and the length of the polyol reactant will dictate the relative yields of 1:1, 2:2 and larger cyclic ligands formed in the equimolar reaction of the thio-bis-(acylating agent) and polyol. In general, the overall yields of cyclic products are enhanced at the expense of linear oligomer as a consequence of the template effect.

Metal ions of such metals as lithium, sodium, potassium, calcium, copper, zinc, iron, and cobalt are useful template reagents; other effective metal derivatives include the alcoholates of titanium, silicon, vanadium and zirconium.

The templating action of those metal species can be achieved by (1) adding the metal salt directly to the reaction mixture or (2) prereacting the metal ion with one of the reactants to form (i) the metal carboxylate of the thio-bis-acylating agent, (ii) the polyhydric alcoholate salt, or (iii) the metal carboxylate of a polyol hemiester which is subsequently bridged with a sulfur halide.

Thus, in accord with synthetic option (1), metal assisted cyclizations can be achieved by simply adding a molar amount of a metal salt, e.g. cupric acetate, to an equimolar mixture of a thio-bis-(acylating reagent), e.g. an $SCl_2$-alkenyl succinic anhydride adduct and a polyol, e.g. tetraethylene glycol, and heating the mixture in a suitable diluent such as tetrahydrofuran or xylene at about 50°–150° C. until esterification (and lactonization) are complete by infrared analysis. Removal of by-product metal halide salt by filtration and solvent removal by rotoevaporation usually affords substantial amounts of the desired ester product. Using similar preparative strategy, the addition of catalytic amounts of tetrabutyl titanate to a mixture of equimolar amounts of thio- bis- lactone acid), e.g., 6,6'-bis-thio-(3,5-carbolactone-heneicosanoic acid) and polyol, e.g., 2,2,6,6-tetramethylol-1-cyclohexanol followed by refluxing the reaction mixture in xylene until ester formation was complete, affords upon work-up, an ester product which is principally a mixture of macrocyclic esters. In the absence of tetrabutyl titanate, the same esterification process affords increased amounts of polymeric ester product.

As indicated above, macrocyclic ester formation via option (2) can be accomplished using several synthetic variations including (i) the reaction of a metal carboxylate salt of a thio-bis-(lactone acid) with an electrophilic glycol analog such as $ClCH_2CH_2(OCH_2CH_2)_nOCH_2CH_2Cl$ wherein n is 0 to 20; (ii) the reaction of a sodium salt of a polyol such as tetraethylene glycol with a sulfur-bridged acylating agent such as thio-bis-(lactone acid chloride) or a $SCl_2$-alkenylsuccinic anhydride adduct; or (iii) the process of forming a metal carboxylate of a glycol hemi-ester, prepared from 2 moles of an alkenylsuccinic anhydride and a molar amount of tetraethylene glycol, and subsequently bridging the hemi-ester with a sulfur halide.

Judging from gel permeation chromatography measurements on the ester products of these processes, it is evident that the presence of a metal ion during esterification tends to increase the yield of macrocycles over ester products from competing linear oligomeric processes. The ability to influence the mode of ester formation with metal salts and solid phases such as silica gel provides a versatile approach to the design of ester products with superior viscosity and performance characteristics.

USE OF THIO-BIS(ALKYL LACTONE ACID ESTERS) AND THIO-BIS-(HYDROCARBYL DIACID ESTERS) AS ADDITIVES IN OLEAGINOUS COMPOSITIONS

The oil-soluble sulfur-bridged lactone ester products of the invention can be incorporated in a wide variety of oleaginous compositions. They can be used in lubricating oil compositions, such as automotive crankcase lubricating oils, automotive transmission fluids, etc., generally within the range of about 0.01 to 20 wt. %, e.g. 0.1 to 10 weight percent, preferably 0.3 to 3.0 weight percent, of the total composition. The lubricants to which the bridged lactone polyol ester products can be added include not only hydrocarbon oils derived from petroleum but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils, mixtures of mineral lubricating oil and synthetic oils in any proportion, etc.

When the products of this invention are used as multifunctional additives having detergent and antirust properties in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as a friction modifier for automatic transmission fluids, the additives of the invention preferably the thio-bis-(hydrocarbyl diacid materials) such as, for example, 6,6'-mono-or di-thio-bis-(3,5-carbolactone-heneicosanoic acid) are present in amounts ranging from about 0.05 to 2 weight percent based on the total weight of the fluid.

When used as an antifoulant in oleaginous, e.g. mineral oil, streams in refinery operations to prevent fouling of process equipment such as heat exchangers or in turbine ils, about 0.001 to 2 wt. % of the inventive additive, preferably a thio-bis-(alkene dioate pentaerythritol ester) will generally be used.

The additive may be conveniently dispensed as a concentrate comprising a minor proportion of the thio additive, e.g., 20 to 90 parts by weight, dissolved in a major proportion of a mineral lubricating oil, e.g., 10 to 80 parts by weight, with or without other additives being present.

In the above compositions or concentrations, other conventional additives may also be present including dyes, pour point depressants, antiwear agents such as tricresyl phosphate or zinc dialkyldithio phosphates of 3 to 8 carbon atoms in each alkyl group, antioxidants, such as N-phenyl -naphthylamine, tert-octylphenol sulfide, 4,4'-methylene bis-(2,6-di-tertbutyl phenol), viscosity index improvers such as ethylene-propylene copolymers, polymethacrylates, polyisobutylene, alkyl fumarate-vinyl acetate copolymers and the like, de-emulsifiers such as polysiloxanes, ethoxylated polymers and the like.

THIYLATED ADDUCTS OF $S_xCl_2$ AND OLEFIN DIACIDS

In another embodiment of the present invention, treatment of $S_xCl_2$alkenyl succinic anhydride adducts and their dehydrohalogenated products with thiylating agents affords thio- or sulfo-substituted derivatives engendered by (a) the displacement of chloride from the adduct by thiol reagents such as $H_2S$, thiol acids such as thioacetic acid, dialkyl dithiophosphoric acid; and alkane thiols, or (b) the addition of one of the above thiol reagents or chloro sulfonic acid or its equivalent ($SO_3$) to a dehydrochlorinated adduct of $S_xCl_2$ and olefin diacid material using an acid-induced or free radical-induced addition to the olefinic unsaturation in the thio-bis (alkene diacid anhydride). This invention will be further understood by reference to the following examples, which include preferred embodiments of the invention.

SYNTHESIS OF ALKENE DIACID REACTANTS

A wide spectrum of alkene diacid materials, amenable to sulfur bridging reactions, can be designed via the reaction of maleic anhydride with an olefin or chlorinated olefin. Both routes to alkenylsuccinic anhydrides involve heating the olefin or chloro-olefin reactant and maleic anhydride together in the presence of catalytic amounts of inhibitor at about 180°-260° C. for 1-24 hours until sufficient adduct is formed. Depending on availability and cost of starting materials, a 1.1-2 fold excess of either reactant can be employed to increase the rate of adduction and yield of alkenyl succinic anhydride. When excess maleic anhydride is employed, varying amounts (10-40% yields) of alkenyl di-, tri-, and poly-succinic anhydrides accompany the mono-adduct together with minor amounts (5-25% yields) of unreacted olefin. Since the mono-adduct is the preferred species for the purpose of this invention, it is advantageous to employ excess olefin in adductions with maleic anhydride. High ratios (1.5-10) of olefin to maleic anhydride afford substantial yields (50-80%) of olefin diacid products comprising Ene structures as

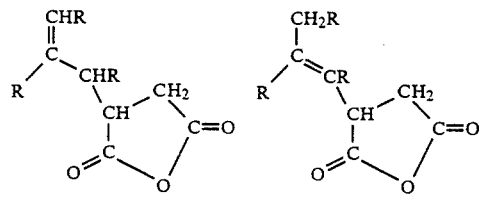

By way of contrast, the reaction of chloroalkenes and maleic anhydride proceeds via an elimination rearrangement pathway to give in part, Diels Alder products comprising such structures as:

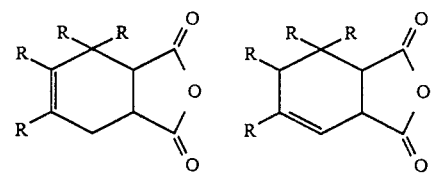

the R group in the Ene or Diels-Alder adducts may be hydrogen, or hydrocarbyl each having from 1 to 400 and more carbons. The most preferred alkenyl succinic anhydrides are those derived from such olefins and chloroalkenes as isobutylene, diisobutylene, chloro diisobutylene, n-octene, tetrapropylene, n-octadecene, polypropylene, polyisobutylene ($M_n \approx 800$ and 1050) and chloropolyisobutylene ($M_n \approx 800$ and 1050). The monochloro olefins, judging from spectral and chemical behavior, are predominantly allylic in character.

The $C_4$-$C_{18}$ olefins and chloro diisobutylene are reacted with maleic anhydride (excess alkene used), at atmospheric pressure or when required, as with isobutylene, and diisobutylene, under pressure (120°-260° C.) for 4-16 hours. The alkenyl succinic anhydride products from $C_4$-$C_{18}$ olefins and chloro diisobutylene were vacuum distilled and heart cuts were taken for sulfur bridging to give model thio-bis-(acylating agents) essentially free of bridged alkenyl di-, and tri-succinic acid anhydrides.

The polyolefin diacid anhydrides were usually prepared by heating about 1-2 moles of maleic anhydride with about 1 mole of polyolefin at about 200°-280° C. in the presence of an inhibitor (1-2 wt. % of PARABAR 441) at 1-200 psi for 8-16 hours. The degree of functionalization was assessed by the (i) saponification number of the polyalkene diacid anhydride, and (ii) chromatographic analysis (on silica gel) of polyolefin diacid for active ingredient present in the reaction mixture. Judging from the saponification numbers and chromatographic analyses for active ingredient, it appears that most polyalkenyl succinic anhydrides contained modest amounts (5-20 wt. %) of bis- and tris-succinic anhydrides and 10-30 wt. % of unreacted polyalkenes.

In the light of the compositional data for the polyalkenyl succinic anhydrides, the present invention also teaches the sulfur halide-induced bridging of alkenyl bis- and tris-succinic anhydrides present in the various PIBSA and chloro-PIBSA reactants. Accordingly, when reference is made to sulfur bridged PIBSA reactants and products, the presence of bridged PIB(SA)$_y$ (where y is 2, 3 or more) is implied in most cases.

The alkenyl succinic anhydride reactants used in designing the thio-bis (acylating) agents of the present invention are featured below:

| | | | Alkenyl | ASA | |
| --- | --- | --- | --- | --- | --- |
| Process | Olefin | Olefin Mol Wt (1) | Succinic Anhydride (ASA) | Sap. Number (2) | Mn (1) |
| Ene | Isobutylene | 57 | Isobutenyl-SA (IBSA) | 720 | 154 |

ALKENYL SUCCINIC ANHYDRIDE (ASA) PRECURSORS TO THIO-BIS-(ACYLATING AGENTS)

-continued

ALKENYL SUCCINIC ANHYDRIDE (ASA) PRECURSORS TO THIO-BIS-(ACYLATING AGENTS)

| Process | Olefin | Olefin Mol Wt (1) | Alkenyl Succinic Anhydride (ASA) | ASA Sap. Number (2) | Mn (1) |
|---|---|---|---|---|---|
| | Di-isobutylene | 112 | Di-isobutenyl-SA (DIBSA) | 553 | 210 |
| | n-octene | 112 | n-octenyl-SA (NOSA) | 550 | 210 |
| | tetrapropylene | 168 | tetrapropenyl-SA (TPSA) | 410 | 228 |
| | octadecene | 252 | octadecenyl-SA (OSA) | 310 | 375 |
| | polypropene | | polypropenyl-SA (PPSA) | 92 | 623 |
| | polyisobutylene | 758 | polyisobutenyl-SA (PIBSA) | 84 | 776 |
| | | 812 | PIBSA | 112 | 757 |
| | | 1050 | PIBSA | 72 | 1080 |
| Diels-Alder | Cl-Diisobutylene | 146 | Cl-DIBSA (3) | | |
| | Cl-polyisobutylene (4.1% Cl) | 800 | Cl-PIBSA (4) | 80 | 751 |
| | | | Cl-PIBSA | 112 | 771 |
| | Cl-polyisobutylene (4.0% Cl) | 1010 | Cl-PIBSA | 103 | 1044 |

(1) Polyolefin and polyalkenylsuccinic anhydride molecular weights determined by Gel Permeation Chromotography (GPC).
(2) Saponification number according to AM-S 500.23.
(3) 3,3,4,5-tetramethyl-1,2,3,6-tetra-hydrophthallic anhydride.
(4) For convenience, Ene and Diels-Alder PIBSA will be identified as PIBSA and Cl-PIBSA, respectively.

A. SYNTHESIS OF MODEL THIO-BIS-(ACYLATING AGENTS)

In the following examples, synthetic procedures are described for bridging the Ene and Diels-Alder products depicted above and their diacid, hemi-ester and diester analogs. Various modes of bridging as a function of bridging agent, bridging temperature, and reactant ratio will be outlined in detail. Moreover, a number of examples will also be put forth to illustrate the conversion at the $S_xCl_2$-olefin diacid adducts into other useful thio-bis-(acylating agents) including bridged alkene diacid anhydrides, and alkyl lactone acids, and esters.

In the first seven examples, the coupling (or bridging) of a model alkene diacid reactant, i.e., isobutenyl succinic anhydride (IBSA) with several bridging agents including $SCl_2$, $S_2Cl_2$, and $SeCl_4$ using various solvents and temperatures; and the conversion of $S_xCl_2$-IBSA adducts into lactones, sulfoxides and sulfones will be elaborated.

EXAMPLE A1

ADDUCT OF $SCl_2$ AND ISOBUTENYL SUCCINIC ANHYDRIDE (IBSA)

Two tenths mole (30.8 g) of isobutenylsuccinic anhydride (IBSA) were dissolved in 100 ml of methylene chloride and 0.1 mole (10.3 g) of $SCl_2$ were added dropwise at 0° C. while under a nitrogen blanket. The reaction was very exothermic, but no HCl evolution was observed. When the addition was completed, the reaction mixture was allowed to warm up to room temperature and stirred for a few hours. The methylene chloride was removed by rotoevaporation at 50° C. for 2 hours. The concentrate featured an infrared spectrum with an intense anhydride carbonyl absorption band at about 5.67 microns and a gel permeation chromogram with a single peak corresponding to the bridged product.

EXAMPLE A2

ADDUCT OF $SCl_2$ AND IBSA AT 100° C.

About 77 g (0.5 mole) of isobutenyl succinic anhydride were dissolved in a very small amount of THF (10 ml) and heated slowly to 100° C. Then, 0.35 mole (40g) of $SCl_2$ were added dropwise for a period of one half hour. When the addition was completed, the reaction mixture was kept at 100° C. for half an hour while stirring under a nitrogen blanket and then nitrogen sparged at 100° C. for another half hour. The infrared spectrum of the product featured a strong anhydride carbonyl absorption band at 5.65 microns; GPC analysis indicated that the product was completely bridged.

EXAMPLE A3

6,6'=THIO-BIS-(5-METHYL-3,5-CARBOLACTONE-HEXANOIC ACID)

Two tenths mole (30.8 g) of isobutenyl succinic anhydride (IBSA) was dissolved in 100 ml of THF and 0.1 mole (10.3 g) of $SCl_2$ were added at 0° C. The reaction mixture was warmed up to room temperature and stirred for four hours. Then, 0.2 mole (3.6 g) of water was added and the reaction mixture was refluxed for several hours to assure complete lactonization. Infrared analysis of the reaction product revealed complete conversion to the desired thio-bis-(lactone acid).

In the same manner, 6,6'-dithio-bis-(5-methyl-3,5-carbolactone-hexanoic acid) was prepared via the reaction of IBSA and $S_2Cl_2$ according to the procedure described above.

EXAMPLE A4

6,6'-THIO-BIS-(5 METHYL-3,5--CARBOLACTONE-HEXANOIC ACID VIA ISOBUTENYL SUCCINIC ACID

Two tenths mole (30.8 g) of IBSA were dissolved in 100 ml of THF and mixed with 0.2 mole (3.6 g) of water. The reaction mixture was refluxed until infrared analysis indicated complete conversion to the diacid product. Then, the solution was cooled to room temperature and 0.1 mole (ea. 10.3 g) of SCl$_2$ was added dropwise for a period of half an hour. An exothermic reaction took place and gas evolution was observed. The mixture was refluxed in THF for 4 hours to assure complete conversion. The infrared analysis of the product confirmed the presence of the desired thio-bis (lactone-acid).

EXAMPLE A5

SULFOXIDE OF THE SCl$_2$-IBSA ADDUCT

Two tenths mole (ca 30.8 g) of isobutenyl succinic anhydride were dissolved in 100 ml of methylene chloride. The resulting solution was stirred at 0° C. and then bridged via the dropwise addition of 10.3 g (ca 0.1 mole) of SCl$_2$. After the addition was completed, the reaction mixture was allowed to stir at room temperature for a few hours.

To the above adduct, 20.2 g (0.1 mole) of 85% meta-chloroperbenzoic acid was added spoonwise for a period of one hour. An external cooling bath was provided to keep the reaction about room temperature. After the addition was completed the clear solution was stirred at room temperature for several hours. During this period the chlorobenzoic acid which precipitated out of solution was filtered. The filtrate was cooled to 0° C. and more acid was filtered. This operation was repeated several times until the infrared spectrum of the filtrate showed the absence of metachlorobenzoic acid.

The CH$_2$Cl$_2$ solution was dripped into a large volume of ether and a white solid formed. The mass spectrum of the product featured a substantial peak at m/e 354 for the dehydrochlorinated bridged sulfoxide product.

EXAMPLE A6

SULFONE OF THE SCl$_2$-IBSA ADDUCT

Oxidation of the SCl$_2$-IBSA adduct described in Example A5 with 0.2 mole of m-chloroperbenzoic acid afforded the desired sulfone derivative.

EXAMPLE A7

ADDUCT OF SELENIUM (IV) CHLORIDE AND IBSA

Three tenths (ca 46.2 g) of IBSA were dissolved in 100 ml of chloroform and 25 g (0.11 mole) of selenium (IV) chloride were added at room temperature while under a nitrogen blanket. The exothermic reaction was maintained about 20° C. via an external cooling bath. No HCl evolution was observed. When the addition was completed, the reaction mixture was allowed to stir at room temperature for 12 hours—the chloroform was rotoevaporated at 100° C. for an hour. The GPC analysis of the residue showed substantial bridging.

The following examples illustrate the (1) sulfenylation of diisobutenyl succinic acid, anhydride, DIBSA hemi-ester, and diester with SCl$_2$ and S$_2$Cl$_2$ at ambient and 100° C. temperature, with and without solvent using reactant ratios of 1:1 and 2:1; and (2) conversions of the S$_x$Cl$_2$-olefin diacid adducts to thio-bis-(alkyl lactone acids and esters) and thio-bis(alkene diacids and diesters).

EXAMPLE A8

DEHYDROCHLORINATED ADDUCT OF SCl$_2$ AND DIISOBUTENYLSUCCINIC ANHYDRIDE

Three-tenths mole (63 g) of diisobutenylsuccinic anhydride (DIBSA) dissolved in 100 ml of methylene chloride was bridged with 0.15 mole (15.5 g) of sulfur dichloride (SCl$_2$) by adding the SCl$_2$ dropwise to the anhydride at about room temperature. External cooling was needed to maintain the exothermic bridging process at about 25° C. The reaction mixture was maintained over nitrogen for 2 days, and subsequently rotoevaporated at about 50° C. for 2 hours. The concentrate featured an IR spectrum with an intense carbonyl absorption band at about 5.67 microns and analyzed for 58.92% carbon, 7.44% hydrogen, 7.84% sulfur and 4.17% chlorine. Theory requires 55.07% C, 6.93% H, 6.12% S, and 13.56% Cl.

EXAMPLE A9

DEHYDROCHLORINATED ADDUCT OF S$_2$Cl$_2$ AND DIISOBUTENYLSUCCINIC ANHYDRIDE

A tenth-mole (21.0 g) of diisobutenylsuccinic anhydride in 150 ml of chloroform and 0.05 mole (6.8 g) of sulfur monochloride in 150 ml of HCCl$_3$ were simultaneously added dropwise to 200 ml of chloroform at about 25° C. After addition, the mixture was stirred at ca 25° C. for 2 days and concentrated by rotoevaporation at ca 25° C.

The concentrate analyzed for 10.31% chlorine and featured a gel chromatogram dominated by a peak corresponding to the S$_2$Cl$_2$-diisobutenylsuccinic anhydride adduct. Refluxing the adduct in dioxane for 24 hours gave a concentrate consisting primarily of 5,5' dithio-bis-(4-neopentyl-3(4)-pentene-1,2-dicarboxylic acid anhydride) which analyzed for 2.12% chlorine. A plausible structure for the thio-bis-(alkene diacid anhydride) product, in parts, is shown below:

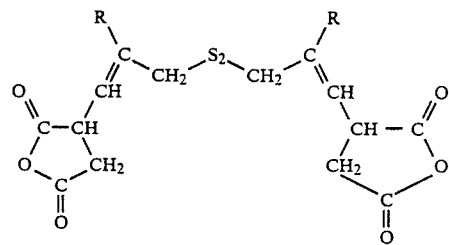

R = neo-pentyl

In a similar manner, diisobutenylsuccinic anhydride (0.05 mole) was sulfenylated with an equimolar amount of sulfur monochloride (S$_2$Cl$_2$). The gel chromatogram of the solvent-free product showed a dominant peak ascribable to the sulfur-bridged anhydride product.

EXAMPLE A10

HIGH TEMPERATURE REACTION OF SCl$_2$ WITH DIISOBUTENYLSUCCINIC ANHYDRIDE

Two-tenths mole (42 g) of diisobutenylsuccinic anhydride being stirred at ca 100° C. under a nitrogen atmosphere, was treated dropwise with 0.1 mole (10.3 g) of sulfur dichloride. The reaction temperature (100° C.) was maintained by the controlled addition of SCl$_2$. Following the completion of SCl$_2$ addition, the stirred mixture was maintained at 100° C. using external heating. Gel chromatography of the product revealed that a substantial portion (ca 66%) of the anhydride was bridged by the $SCl_2$. Complete bridging could be achieved by the further addition of $SCl_2$ to the mixture.

EXAMPLE A11

ADDUCT OF $SCl_2$ AND DIISOBUTENYLSUCCINIC ANHYDRID( VIA EQUIMOLAR REACTION

Bridging of 0.05 mole (10.5 g) of diisobutenylsuccinic anhydride (dissolved in 50 ml of $CH_2Cl_2$) was effected by the dropwise addition of an equimolar amount (0.05 mole, 5.2 g) of $SCl_2$ to the anhydride at ca 25° C. The concentrated product featured an IR spectrum with a strong anhydride carbonyl absorption band at 5.67 microns and a gel chromatogram with an intense band corresponding to the bridged anhydride product.

EXAMPLE A12

6,6'THIO-BIS-(5-NEOPENTYL-3,5-CARBOLACTONE-HEXANOIC ACID)

Two tenths mole (42.0 g) of diisobutylene succinic anhydride (DIBSA) was dissolved in 100 ml of THF and 0.1 mole (10.3 g) of $SCl_2$ were added. During addition, the reaction temperature climbed to about 35° C. and HCl evolution occurred. The mixture was refluxed for four hours and then heated to 100° (THF distilled off) for two more hours to effect complete dehydrohalogenation.

The residue was cooled and dissolved in THF and 0.2 mole of water and two drops of concentrated sulfuric acid were added. The mixture was refluxed for several hours. Infrared analysis revealed complete conversion to the desired thio-bis-lactone acid pictured below.

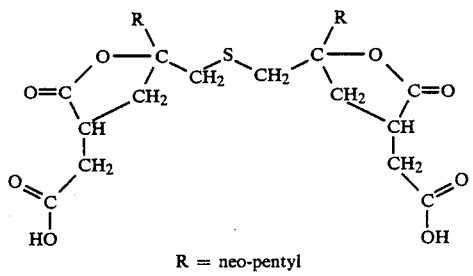

R = neo-pentyl

EXAMPLE A13

6,6'-DITHIO-BIS-(5-NEOPENTYL-3,5-CARBOLACTONE-HEXANOIC ACID)

A tenth mole (21 g) of diisobutenylsuccinic acid was prepared via hydrolysis of the corresponding anhydride in refluxing tetrahydrofuran (THF). After IR analysis indicated complete conversion to said diacid, the reaction temperature was elevated to 95° C. by distilling off a sufficient volume of THF solvent. While maintaining a temperature of ca. 95°-100° C., 0.05 mole (6.9 g) of sulfur monochloride was added dropwise to the stirred solution. HCl evolution was noted. Rotoevaporation of the reaction mixture gave a concentrate of the product which featured an IR spectrum dominated by an intense lactone carbonyl absorption band at 5.68 microns. The gel chromatogram of the residue show a large band ascribable to the desired sulfur-bridged lactone acid.

EXAMPLE A14

6,6'-THIO-BIS-(5-NEOPENTYL-3,5-CARBOLACTONE-HEXANOIC ACID)

Two tenths mole (42.0 g) of DIBSA was dissolved in 100 ml of THF and 0.1 mole (10.3 g) of $SCl_2$ were added. During addition the reaction temperature climbed to about 35° C. and HCl evolution occurred. The mixture was refluxed for four hours and then heated to 100° (THF distilled off) for two more hours to effect complete dehydrohalogenation.

The residue was cooled and dissolved in THF and 0.2 mole of water and two drops of concentrated sulfuric acid were added. The mixture was refluxed for several hours. Infrared analysis revealed complete conversion to the title thio-bis-(lactone acid).

EXAMPLE A15

SULFUR BRIDGED LACTONE ESTER REACTANTS

DIMETHYL 6,6'-THIO-BIS-(5-NEO-PENTYL-3,5-CARBOLACTONE-HEXANOATE)

A tenth mole of mono-methyl diisobutenylsuccinate was dissolved in 100 ml of xylene and 0.05 mole of $SCl_2$ was added dropwise to the stirred xylene solution maintained at ca. 25° C. The mixture was refluxed overnight and rotoevaporated for three hours at 90° C. IR analysis revealed that the hemi-ester/$SCl_2$ adduct was completely converted to the desired thio-bis-lactone methyl ester. A plausible structure for the sulfur-bridged bis-lactone is shown below:

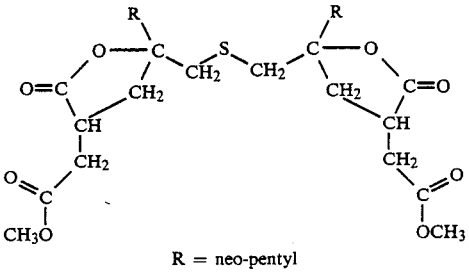

R = neo-pentyl

EXAMPLE A16

TETRAMETHYL 5,5'-DITHIO-BIS-(4-NEO-PENTENE-1,2-DICARBOXYLATE)

A tenth mole (25.6 g) of dimethyl diisobutenyl succinate in 100 ml $CH_2Cl_2$ was treated dropwise with 0.05 mole (6.8 g) or $S_2Cl_2$ at room temperature. After addition, the reaction mixture was stirred at room temperature for several hours and rotoevaporated at 50° C. for 2 hours. The concentrate featured a gel chromatogram with a dominant peak consistent with the sulfur-bridged ester product, dithio-bis-(alkenylsuccinic acid dimethyl ester), corresponding to a $M_n$ of about 400. Heating the adduct at 225° C. hours afforded a material with a gel chromatogram similar to that prior to heating. Clearly, the thermolytic conditions imposed on the bridge structures failed to cleave the sulfur-linked acid esters, and demonstrates the stability of the 5-bridged esters towards the thermal conditions imposed during the esterification of the bridged structures.

The following examples illustrate the bridging of diisobutenyl succinic anhydride (DIBSA) via successive thiolation and oxidation reactions.

EXAMPLE A17

TETRAMETHYL 4,4'-DITHIO-BIS-(4-NEOPENTYL-1,2PENTANE-DICARBOXYLATE)

Two tenths mole (42 g) of diisobutenylsuccinic anhydride was dissolved in 200 ml of $CH_2Cl_2$ and cooled to $-70°$ C. Ten grams of gaseous hydrogen sulfide were then condensed into the reactor at $-70°$ C. The stirred reaction mixture was subsequently treated with gaseous $BF_3$ (1 bubble/sec) for 3 hours at $-70°$ C. The clear colorless solution turned yellow after 1 hour, and upon warming to room temperature, assumed a dark red color. The solvent was removed and the reaction mixture heated to 120° C. for 1 hour. IR analysis of the mixture showed the presence of thiolactone acid. Further reaction with methanol at 80° C. for 1 hour gave the thiolactone lactone ester (shown below) which was dissolved in ether, washed several times with aqueous $NaHCO_3$, and dried over $MgSO_4$.

Vacuum distillation of the residue afforded 29 g of a fraction, b.p. 128°–130° C. (0.04 mm), which featured an IR spectrum with strong carbonyl absorption bands at 5.73 and 5.86 microns and a proton spectrum consistent with a 5-ring thiolactone ester. Elemental analyses showed 60.59% carbon, 8.53% hydrogen and 12.00% sulfur. Theory requires 60.42% C, 8.58% H and 12.41% sulfur. The proposed structure for the thiolactone ester is featured below:

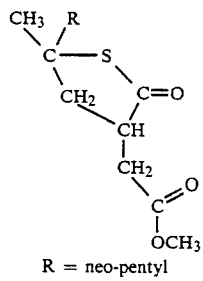

R = neo-pentyl

Oxidation of said thiolactone ester with a mole equivalent of t-butyl hypochlorite in methanol afforded the tittle dithio-bis-ester product in high yields.

EXAMPLE A18

TETRAMETHYL 5,5'-DITHIO-BIS-(4-NEO-PENTYL-1,2-(PENTANEDICARBOXYLATE)

A tenth mole (7.6 g) of thioacetic acid and 0.05 mole (10.5 g) of diisobutenylsuccinic anhydride were dissolved in 30 ml of ether and stirred at room temperature overnight. Distillation of the mixture freed of solvent gave a fraction (8.0 g) boiling at 180°–185° C. (0.1 mm). The IR spectrum of the product recrystallized from ether/pentane (m.p. 72°–73° C.) featured intense anhydride and thiol ester carbonyl absorption bands at 5.64 and 5.95 microns. The crystalline product analyzed for 59.03% C, 7.57% H and 10.99% S. Theory requires 58.70% C, 7.57% H and 11.20% S. The proton and carbon magnetic spectra were consistent with the structure of the thioacetyl anhydride intermediate as shown below:

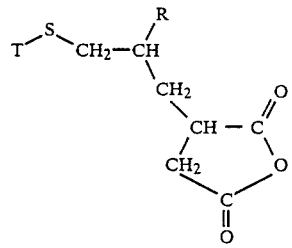

Oxidation of said thioacetyl anhydride was smoothly effected via the dropwise addition of 0.02 mole (2.7 g) of sulfuryl chloride to ca 50 ml of a methanol solution of 0.02 mole (5.72 g) of the thioacetyl anhydride. The addition produced an exotherm and the reaction temperature peaked at ca 50° C. The mixture was stirred at ambient temperatures for about an hour. Gel permeation chromatography (GPC) of the reaction mixture indicated that oxidative coupling was ca 80% complete; accordingly, additional $SO_2Cl_2$ (ca 0.5 g) was added until the GPC of the reaction mixture showed only a product peak. Upon standing, the reaction mixture crystallized. The solids recrystallized from ether/pentane melted at 82°–83° C. and, featured: an IR spectrum with a dominant carbonyl band at 5.72 microns, a proton spectrum with a double methyl proton signal centered at 6.3 tau, and a mass spectrum with a molecular ion peak at 578. The data are completely consistent with the bridged structure shown below. The product analyzed for 58.24% carbon, 8.48% hydrogen, 10.99% sulfur, and 22.24% oxygen. Theory requires: 58.09% C; 8.70% H; 11.08% S and 22.11% O.

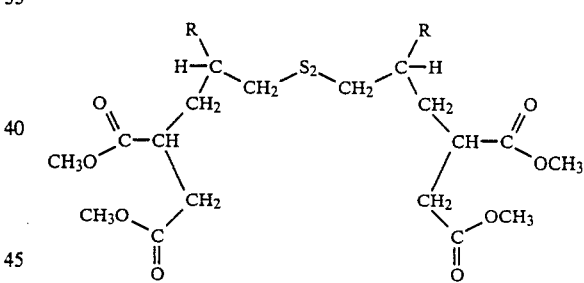

wherein R is neopentyl.

The following examples describe unsuccessful attempts to prepare stable bridged derivatives of Ene and Diels-Alder adducts (DIBSA and Cl-DIBSA) via sulfurization with elemental sulfur. Also illustrated is the attempted Ene reaction of alkenyl disulfide with maleic anhydride, which afforded 2-alkylthiasuccinic acid anhydride rather than the desired thio-bis-(acylating agent).

EXAMPLE A19

SULFURIZED DIISOBUTENYL SUCCINIC ANHYDRIDE

A mixture of 10.5g and (0.05 mole) of diisobutenylsuccinic anhydride (DIBSA) and elemental sulfur (0.05 mole, 1.6 g) was heated to 205° C. and maintained at this temperature with magnetic stirring for 5 hours. IR analysis of the reaction mixture showed the appearance of a strong absorption band at 5.9 microns (ascribable possibly to thioanhydride) and a shift in the C=C absorption band from 6.05 to 6.22 microns (attributable possibly to a sulfur-induced isomerization of the C=C double bond). Gel permeation chromatography (GPC) featured an intense peak maximum corresponding to that observed for diisobutenylsuccinic anhydride. A peak in the gel chromatogram corresponding to sulfur-bridged diisobutenylsuccinic anhydride products, i.e., thio-bis-(diisobutyl succinic anhydride) was conspicuously absent.

EXAMPLE A20

SULFURIZATION OF Cl-DIBSA

A mixture of 3,3,4,5-tetramethyl-1,2,3,6-tetrahydrophthallic anhydride (3.6 g, 0.017 mole), 0.27 g (.0085 mole) of sulfur and 20 ml of dichlorobenzene was heated to reflux for about 72 hours. The product was freed of dichlorobenzene by rotoevaporation; the gel chromatography of the residue revealed a peak maximum which coincided with the starting material.

EXAMPLE A21

REACTION PRODUCT OF DIISOBUTENYL SULFIDE AND MALEIC ANHYDRIDE

A half mole (144g) of diisobutenyl disulfide (prepared via addition of $S_2Cl_2$ to 2,4,4-trimethyl-2-pentene) and a mole (98 g) of maleic anhydride were combined and heated gradually to about 170° C. and maintained at this temperature (with stirring) for 3 hours. The clear, orange-colored reaction mixture turned pitch black during heating, and solids began to deposit on the walls of the reactor. Only part (ca 115 g) of the hot reaction mixture could be decanted. The black, resinous-like mass adhering to the reactor weighed ca 127 g. Vacuum distillation of the decanted reaction mixture afforded about 14g of product, b.p. 115-120 (0.5 mm). The IR spectrum of the distillate featured characteristic carbonyl absorption bands for an anhydride product and analyzed for 18.15% sulfur.

The following examples relate to the bridging of Diels-Alder adducts with $SCl_2$ and $S_2Cl_2$ and the conversion of the $S_xCl_2$-olefin diacid anhydride to the corresponding thio-bis-(lactone acid).

EXAMPLE A22

Two-tenths (30.4 g) mole of cis-1,2,3,6-tetrahydrophthalic anhydride (cis-4-cyclohexene-1,2-dicarboxylic anhydride) was dissolved in chloroform (200 ml) and 0.1 mole (10.3 g) of $SCl_2$ were added dropwise to the well stirred solution at room temperature. The $SCl_2$ addition increased the temperature to 53° C. and the addition was completed at about 53° C. Midway during $SCl_2$ addition the solution turned hazy and some solids separated from solution. After addition the mixture was allowed to cool and the solids (20 g) were isolated by filtration. The solid product featured an IR spectrum with strong anhydride carbonyl absorption, melted at 177°-178° C., and analyzed for 46.88% C, 4.22% H, 7.68% S, and 14.93% Cl. Theory for the adduct ($C_{16}H_{16}Cl_2O_6S$) requires 47.18% C, 3.96% H, 7.87% S, and 17.41% Cl.

About 10.2 g (0.025 mole) of the adduct of cis 1-2,3,6-tetrahydrophthalic anhydride and $SCl_2$ were dissolved in 100 ml of THF and mixed with 1 g of water and two drops of concentrated sulfuric acid. The mixture was refluxed in THF for four hours, then the THF was distilled off and replaced by p-dioxane. The dioxane solution was refluxed for about 24 hours. The dioxane was stripped and the residue was dissolved in a mixture of methylene chloride and ether. A white solid separated. The solid featured an infrared spectrum consistent with the desired lactoneacid product.

EXAMPLE A23

A mole (152 g) of cis-1,2,3,6-tetrahydrophthalic anhydride (cis-4 cyclohexene-1,2-dicarboxylic anhydride) was dissolved in 400 ml of chloroform and 0.50 mole (68 g) of sulfur monochloride were added dropwise to the well stirred solution at room temperature. Initially the $S_2Cl_2$ addition did not produce an exothermic reaction, but the reaction temperature rose to about 33° C. by the end of the addition, the solution was allowed to stir at room temperature for 8 hours, some solid separated during this period. The solid was filtered and yielded 166 g of a white crystalline material which melted at 154°-156° C. and analyzed for 44.03 wt. % C, 4.12 wt. % H, 14.75 wt. % S and 15.43 % Cl. The solid product featured an IR with strong anhydride carbonyl absorption. The filtrate was evaporated obtaining an oily residue with an infrared analysis and GPC similar to the solid product.

EXAMPLE A24

About 11.0 g (0.025 mole) of the adduct of cis 1-2,3,6-tetrahydrophthalic anhydride and $S_2Cl_2$ were dissolved in 100 ml of THF and mixed with 1 g of water and two drops of concentrated sulfuric acid. The mixture was refluxed in THF for four hours, then the THF was distilled off and replaced by p-dioxane. The dioxane solution was refluxed for about 24 hours. The dioxane was stripped and the residue was dissolved in a mixture of methylene chloride and ether. A white solid separated. The solid featured an infrared spectrum consistent with the desired lactone-acid product.

EXAMPLE A25

SULFENYLATION OF Cl-DIBSA WITH $SCl_2$

Approximately 2.08 g (ca 0.01 mole) of 3,3,4,5-tetramethyl-1,2,3,6-tetrahydrophthallic anhydride were dissolved in 50 ml of anhydrous ether and stirred at room temperature under a nitrogen blanket. Then, 0.5 g (ca 0.005 mole) of $SCl_2$ were added dropwise. No HCl evolution was observed. The reaction mixture was stirred at room temperature overnight and then added dropwise into a large volume of pentane. It yielded 1.2 g of a white solid which showed to be the sulfur-bridged product of the nitrogen, producing 1.4 g of an oily substance. The GPC of the oily material showed mainly sulfur-bridged anhydride product.

In the ensuing examples, the bridging of n-octenyl-succinic anhydride (NOSA), diacid, hemiester and silica gel-bound NOSA with such sulfenylating agents as $SCl_2$, $S_2Cl_2$, $Se_2Cl_2$ 1,2-ethane-bis-sulfenyl chloride, 1,3,4-thiadiazole-2,5-bis-sulfenyl chloride, and a novel alkyl sulfenate ester-HCl combination reagent using various experimental conditions, are elaborated.

Methods for converting the $S_xCl_2$-NOSA adducts to thio-bis (lactone acids and esters) are also described.

EXAMPLE A26

ADDUCT OF $SCl_2$ AND n-OCTENYLSUCCINIC ANHYDRIDE

Three moles (630 g) of n-octenylsuccinic anhydride (NOSA) were diluted in a liter of $CH_2Cl_2$ and stirred at room temperature. Then 1.5 moles (154 g) of $SCl_2$ in 500 ml of $CH_2Cl_2$ were added dropwise. The exothermic reaction peaked to 50° C. initially and external cooling was applied to maintain reaction temperature at about 25° C. No HCl evolution occurred. After stirring the reaction mixture for an hour after the SCl₂ addition, the solvent was removed by evaporation with a mild stream of nitrogen. The solid that separated from solution during solvent evaporation was isolated (40 g) and after being recrystallized from CH₂Cl₂, melted at 149149°–150° C. and analyzed for 55.45% C, 7.17% H, 5.73% S and 11.4% Cl.

The adduct, $C_{24}H_{26}O_6SCl_2$ requires 55.06% C, 6.93% H, 6.13% S, and 13.55% Cl. The infrared spectrum featured an intense anhydride absorption at 5.67 microns, and a proton spectrum consistent with the structure shown The concentrate obtained from the supernatant weighed 745 g and featured an IR spectrum similar to that shown for the solid. The yield of anhydride-SCl₂ adduct was virtually quantitative. A structure for one of the dominant bridged isomers formed in the SC12-anhydride reaction is depicted below:

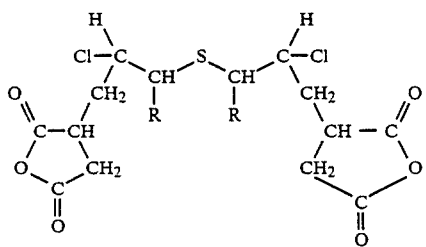

R = C₅H₁₁ (n-pentyl)

EXAMPLE A27

S₂Cl₂-n-OCTENYLSUCCINIC ANYDRIDE (NOSA) ADDUCT

A mole (210 g) of n-octenylsuccinic anhydride was dissolved in a liter of ether and a half mole (67.5 g) of sulfur monochloride (S₂Cl₂) was added dropwise to the stirred solution at room temperature. An exothermic reaction occurred and the addition was completed under refluxing conditions. The reaction mixture was stirred overnight and then concentrated by rotoevaporation at 50° C. for 2 hours. The product featured an IR spectrum with a prominent anhydride carbonyl band at 5.65 microns, and analyzed for 49.33% C, 6.04% H, 10.7% S and 12.6% Cl. Theory for the S₂Cl₂-n-octenyl-succinic anhydride adduct ($C_{24}H_{36}Cl_2O_6S_2$) requires 51.88% C, 6.53% H, 11.54% S, and 12.76% Cl.

EXAMPLE A28

6,6'-THIO-BIS-(3,5-CARBOLACTONE-UNDECANOIC ACID)

228 g (1.0 mole) of n-octenyl succinic acid, prepared via the hydrolysis of NOSA at 80° C., were dissolved in 200 ml of tetrahydrofuran (THF) and stirred at room temperature while 52 g (0.5 mole) of SCl₂ were added dropwise. The reaction was exothermic and HCl evolution was observed during and after the addition which took about one hour. When the addition was completed, the reaction mixture was allowed to stir at room temperature overnight; a white solid formed upon standing. The solid was filtered, collected and dried (43 g). The infrared analysis of the white powder showed it to be desired thio-bis-(lactone acid) which analyzed for 59.81% C, 7.68% 26.42% O, and 6.52% S (theory requires: 59.23% C, 7.87%, 26.30% O and 6.59% S). The filtered reaction mixture was then refluxed in THF for a few hours to effect complete reaction. Further work-up of the reaction mixture afforded more white solids amounting to a quantitative yield of product. In accord with expectations, GPC analysis featured a single band with a peak maxmum of $M_n$ 480; and mass spectral analysis revealed a molecular ion at m/e 486, in harmony with the proposed structure shown below:

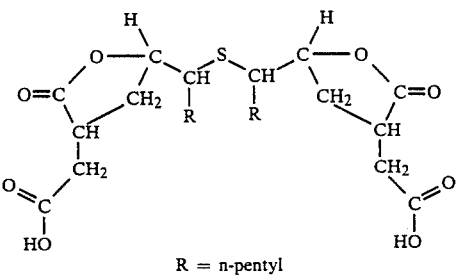

R = n-pentyl

EXAMPLE A29

ADDUCT OF 1,2-ETHANE-BIS-SULFENYL CHLORIDE AND N-OCTENYLSUCCINIC ANHYDRIDE

A tenth mole (21.0 g) of n-octenylsuccinic anhydride dissolved in 100 ml of methylene chloride was bridged with 0.05 mole (8.2 g) of 1,2-ethane-bis-sulfenyl chloride via the dropwise addition of the latter to the anhydride at 0° C. over a 15-minute period. The reaction mixture was stirred overnight and rotoevaporated The IR spectrum of the concentrate featured a strong anhydride carbonyl absorption band at 5.65 microns. The gel permeation chromatogram of the product featured a single peak corresponding to the bridged adduct.

Treatment of the adduct product with a tenth mole of water at 70° C. for an hour afforded the corresponding lactone acid, 6,11-dipentyl-3,5,:14,12-bis-carbolactone-7,10-dithiahexadecane-1.16-dioxic acid in quantitative yield. The IR spectrum of the lactone product featured strong lactone and carboxylic acid carbonyl absorption bands at 5.68 and 5.88 microns.

EXAMPLE A30

ADDUCT OF SELENIUM (I) CHLORIDE AND NOSA

Three tenths mole (63.0 g) of NOSA were dissolved in 100 ml of CHCl₃ and 34.5 (0.15 mole) of selenium (I)

chloride were added dropwise at room temperature. The reactor mixture was stirred at room t temperature for 24 hours. The CHCl₃ was rotoevaporated until constant weight and the residue showed by GPC a maximum peak corresponding to the bridged product.

EXAMPLE A31

DIMETHYL 6,6'-THIO-BIS-(3,5-CARBOLACTONE-1-UNDECANOATE)

A half-mole of the adduct of SC12 and n-octenylsuccinic anhydride was added to 500 ml of xylene containing 32 g of methanol. The mixture was allowed to stir overnight and heated to reflux for about four hours. The product was then rotoevaporated for three hours at 70°–80° C. The final product featured an IR spectrum with intense lactone and ester carbonyl absorption at 5.63 and 5.78 microns, and analyzed for 60.48% carbon, 8.30% hydrogen, and 6.48% sulfur. The thio-bis-lactone ester ($C_{26}H_{42}O_8S$) requires 60.67% C, 8.23% H and 6.23% S.

The same ester lactone was easily prepared via the addition of $SCl_2$ to the mono-methyl ester of n-octenyl succinic acid.

EXAMPLE A32

DIMETHYL 6,6'-DITHIO-BIS-(3,5-CARBOLACTONE--UNDECANOATE)

Four-tenths mole of the adduct of $S_2Cl_2$ and n-octenylsuccinic anhydride and 0.8 mole (25.6 g) of methanol were dissolved in 200 ml of chloroform and stirred at room temperature for four days, refluxed in 16 hours, and rotoevaporated at 80° C. for three hours. The product showed an IR spectrum with intense lactone and ester carbonyl bands and analyzed for 57.19% carbon, 7.93% hydrogen, and 10.54% sulfur. Theory for the methyl ester product ($C_{26}H_{42}O_8S_2$) requires 57.11% carbon, 7.74% hydrogen and 11.73% sulfur.

The same lactone ester could be readily prepared via the addition of $S_2Cl_2$ to the monomethyl ester of n-octenylsuccinic acid.

6,6'-DITHIO-BIS-(3,5-CARBOLACTONE-UNDECANOIC ACID)

A half-mole 114 g) of n-octenylsuccinic acid (prepared via hydrolysis of n-octenylsuccinic anhydride at 80°) in 500 ml of chloroform was treated dropwise with a quarter mole (37.8 g) of sulfur monochloride ($S_2Cl_2$) at room temperature. The mixture was then refluxed for several hours (strong HCl evolution). Infrared analysis of the reaction mixture showed the presence of the desired lactone acid. The corresponding monothio product can be prepared in the above-described manner with $SCl_2$.

EXAMPLE A34

THIO-BIS-(LACTONE ACID) VIA ADDITION OF $SCl_2$ TO SILICA GEL-BOUND N-OCTENYLSUCCINIC ANHYDRIDE

About 42 g (0.2 mole) of NOSA were dissolved in 200 ml of n-octane admixed with about 200 g of silica gel. An infrared spectrum of the octane layer showed that all of the NOSA had been adsorbed to the silica gel. Then, 10.3 g (0.1 mole) of SC12 were added dropwise to the slurry, and an exothermic reaction took place. The mixture was stirred at room temperature for 2 hours and 3.6 g (0.2 mole) of water were added. The well-stirred mixture was refluxed in octane for about 8 hours. The n-octane was decanted and the silica gel was extracted three times with 200 ml aliquots of THF (tetrahydrofuran). The THF was evaporated and a semisolid product was obtained. The infrared and MS spectral data fully confirmed that the product was the desired 6,6'-thio-bis-(3,5 carbolactone-undecanoic acid).

EXAMPLE A35

THIO-BIS-(LACTONE ESTER) VIA THE HCl-INDUCED REACTION OF DIISOPROPOXY DISULFIDE WITH NOSA

About 42 g (0.2 mole) of NOSA were dissolved in 100 ml of THF and stirred at room temperature under a nitrogen blanket, while 18.2 g (ca 0.1 mole) of diisopropoxy disulfide were added. Then, hydrogen chloride gas was slowly bubbled into the stirred solution at room temperature for about 3 minutes. An exothermic reaction took place upon the addition of gaseous HCl. The reaction mixture was stirred at room temperature for a few minutes and then refluxed in THF with one drop of concentrated sulfuric acid for about 8 hours. The THF was stripped and an oily residue was obtained. The residue featured an infrared spectrum characteristic of a sulfur bridged lactone ester. GPC analysis indicated complete bridging.

EXAMPLE A36

BRIDGING OF NOSA VIA SULFENYLATION WITH 1,3,4-THIADIAZOLE-2,5-BIS-SULFENYL CHLORIDE

Two-tenth mole (42 g) of n-octenyl succinic anhydride (NOSA) were dissolved in 100 ml of CHCl₃ and 0.1 mole (21.9 g) of 1,3,4-thiadiazole 2,5=bis-sulfenyl chloride in 100 ml of chloroform were added dropwise for a period of 15 minutes. An external cooling bath was provided to keep the addition at room temperature. The reaction mixture was then stirred at about 25° C. overnight. The solution was filtered and the filtrate was concentrated with a stream of nitrogen. The oily residue featured an infrared spectrum with strong anhydride carbonyl absorption band at 5.65 microns. GPC analysis revealed that complete bridging had been achieved. Spectral analyses were in full accord with the desired thio-bis-(acylating agent).

In the examples that follow, the sulfur bridging of tetrapropenylsuccinic anhydride (TPSA) and octadecenylsuccinic anhydride (OSA) and its diacid analog, with $SCl_2$ and $S_2Cl_2$ using various temperatures and solvents, will be described.

EXAMPLE A37

ADDUCT OF $S_2Cl_2$ AND TETRAPROPENYLSUCCINIC ANHYDRIDE

A mole (266.4 g) of tetrapropenylsuccinic anhydride dissolved in 300 ml of $CH_2Cl_2$ and a half mole (68 g) of sulfur monochloride in 200 ml of CH2Cl2 were added dropwise and simultaneously into a reactor containing 500 ml of CH₂Cl at about 25° C. and then the reaction mixture was stirred overnight. Removal of solvent by evaporation gave a concentrate containing 4.73% chlorine and featuring an infrared spectrum with an intense anhydride carbonyl absorption band at 5.65 microns. Rotoevaporation of the concentrate at 100° C. for 4 hours gave an adduct which analyzed for 3.19% chlorine and gave a gel permeation chromatogram characterized by a dominant band for the sulfur-bridged anhydride product.

EXAMPLE A38

DEHYDROCHLORINATED ADDUCT OF SCl$_2$ AND n-OCTADECENYL SUCCINIC ANHYDRIDE (OSA)

Two hundred grams (0.57 mole) of n-octadecenylsuccinic anhydride were dissolved in 150 ml of chloroform. The resulting solution was stirred at room temperature and then bridged via the dropwise addition of 29.4 g (0.286 mole) of sulfur dichloride. The bridging event was sufficiently exothermic to reflux the chloroform diluent. Evolution of HCl gas was noted during the SCl$_2$ addition. Refluxing was continued for several hours after addition by applying external heating to the reactant. Rotoevaporation of the mixture for 2 hours at 100° C. afforded the S-bridged anhydride adduct. Gel permeation chromatography revealed that coupling with SCl$_2$ was virtually complete. The S-coupled anhydride adduct featured an intense carbonyl absorption band at 5.68 microns and analyzed for 4.65% sulfur and 3.88% chlorine. The chlorine analysis indicates that the adduct had undergone extensive dehydrochlorination.

EXAMPLE A 39

ADDUCT OF S$_2$Cl$_2$ AND OCTADECENYLSUCCINIC ANHYDRIDE

Two hundred grams (0.57 mole) of n-octadecenyl succinic anhydride dissolved in 150 ml of chloroform was bridged via the dropwise additive of 8.6 g (0.286 mole) of sulfur monochloride (S$_2$Cl$_2$) at room temperature. The bridging reaction caused a gradual exotherm (solvent began refluxing) accompanied by the evolution of HCl. Refluxing was continued after S$_2$Cl$_2$ addition for about 24 hours. Rotoevaporation at 100° C. for several hours gave a concentrate which featured a gel permeation chromatogram consistent with the expected sulfur-bridged anhydride adduct product. The adduct analyzed for 6.99% sulfur, and 5.29% chlorine, and featured an IR spectrum dominated by an anhydride carbonyl absorption band at 5.67 microns.

The chlorine analysis is consistent with a mixture comprising the dichlorosulfide, mono-chlorosulfide and unsaturated sulfide products.

EXAMPLE A40

6,6'-THIO-BIS-(3,5 CARBOLACTONE-HENEICOSANOIC ACID)

Two-tenths mole (73.6 g) of octadecenylsuccinic acid was dissolved in 500 ml ether and a tenth mole (10.3 g) of SCl$_2$ was added dropwise to the stirred ether solution at about 25° C. The addition was exothermic (ether refluxed) and HCl evolution occurred. The mixture was refluxed for about 8 hours. Upon cooling solids separated from solution. The solid product featured an infrared spectrum with prominent lactone and carboxylic acid carbonyl absorptions at 5.62 and 5.82 microns, melted at 158°–163°, and analyzed for 69.01% C, 10.17% H, 4.37% S and 16.74% O. Gel permeation chromatography revealed that coupling of the diacid with SCl$_2$ was virtually complete to the lactone acid structure. Theory for the thio-bridged lactone acid (C$_{44}$H$_{78}$O$_8$S) requires 68.88% C, 10.25% H, 4.18% S and 16.69% O.

Further refluxing the supernatant gave four more crops of product with a combined weight of 50 g. The yields were quantitative. The proposed structure for the title thio-bis-(lactone alkanoic acid) is illustrated

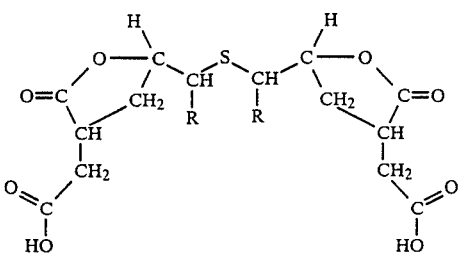

wherein R is n-c$_b$ $_{15}$H$_{31}$.

EXAMPLE A41

6,6'-DITHIO-BIS-(3,5-CARBOLACTONE-1-HENEICOSANOIC ACID)

Two-hundred grams (0.54 mole) of n-octadecenyl succinic acid were dissolved in a liter of CHCl$_3$ and 36.7 g (0.272 mole) of sulfur monochloride (S$_2$Cl$_2$) were added dropwise to the stirred solution at room temperature. The exothermic process was accompanied by vigorous HCl evolution. After refluxing the mixture for about eight hours, the solution was cooled and solids separated. Filtration gave 19 g of solid (m.p. 131°–136° C.) which featured an IR spectrum with intense carbonyl bands at 5.62 and 5.72 microns, and analyzed for 66.42% C, 9.63% H, and 8.22% S. Theory for the adduct (C$_{44}$H$_{78}$O$_8$S$_2$) requires 66.12% C, 9.84% H, and 8.02% S. Rotoevaporation of the supernatant gave a solid product in high yield.

B. SYNTHESIS OF MACRO THIO-BIS-(ACYLATING AGENTS)

The following Examples describe the sulfenylation of polyisobutenyl succinic acids, anhydrides and hemiesters with SCl$_2$ and S$_2$Cl$_2$ to give thio-bis-(acylating agents).

Several examples also teach the use of solid phase synthesis wherein silica gel-bound PIBSA is successively (a) bridged via sulfenylation with sulfur halide and (b) lactonized directly on the solid phase to afford thio-bis-(lactone acids and esters).

EXAMPLE B1

THIO-BIS-(POLYISOBUTYL LACTONE ACID)

Approximately 130 g of polyisobutenyl succinic acid M$_n$ 776, prepared via hydrolysis of PIBSA having a Sap. No. of ca 84 were dissolved in 400 ml of chloroform and 0.05 mole (5.3 g) of SCl$_2$ was added dropwise to the stirred solution. After refluxing the mixture overnight, two drops of sulfuric acid were added, the solvent was stripped off, and the mixture heated at about 100° C. overnight. The product featured an infrared spectrum with strong carbonyl absorption bands in the 5.6–5.8 micron region and analyzed for 1.69% sulfur and 0.09% chlorine. The IR spectrum of the diethylamine-treated product revealed a strong lactone carbonyl band at 5.63 microns.

EXAMPLE B2

THIO-BIS-(POLYISOBUTYL LACTONE ACID)

Ca. 0.1 mole (130 g) of PIBSA [M$_n$ of 776] of 776 having a Sap. No. of ca. 84 was dissolved in 100 ml of dioxane and 0.05 mole (5.3 g) of SC12 was added dropwise to the well-stirred solution at ca. 25° C. The mixture was then refluxed for four hours (HCl evolution noted). At this point, g of water acidified with three drops of concentrated sulfuric acid were added and the mixture was further refluxed for 24 hours. The mixture was filtered through basic Celite and rotoevaporated at 90° C. for several hours. The concentrate featured an IR spectrum with strong absorption bands in the 5.6–5.8 micron region, and analyzed for 1.55% sulfur and 0.09% chlorine.

EXAMPLE B3

DITHIO-BIS-(POLYISOBUTYL LACTONE ACID)

Five hundred grams (0.385 moles) of PIBSA having an (Mn) of 776 and a Sap. No. of 84 were dissolved in 60 ml of methylene chloride and cooled to 0° C. While stirring at 0° C. under a nitrogen blanket, 26 g (0.192 moles) of sulfur monochloride were added dropwise over a period of half hour. The reaction mixture was allowed to warm up to room temperature and stirred for about ten hours.

One-half of this product was diluted in 100 ml of p-dioxane and 6.9 g of water (ca. 0.38 moles) were slowly added. The reaction mixture was refluxed for ten hours in the presence of a catalytic amount of sulfuric acid (HCl evolution occurred during reflux). Thereafter, the solvent was removed by rotoevaporation and the mixture further heated to 130°–140° C. for one hour. The product featured an infrared spectrum with strong absorption bands in the 5.6–5.8 micron region (lactone acid) and analyzed for 2.43 wt. % sulfur and 0.05 wt. % Cl. The IR spectrum of the diethylamine treated product revealed a strong lactone carbonyl band at 5.63 microns.

EXAMPLE B4

DITHIO-BIS-(POLYISOBUTYL LACTONE ACID METHYL ESTER)

A tenth mole (130 g) of polyisobutenylsuccinic anhydride (PIBSA) of $M_n$ 776 and having a Saponification Number of about 84 was dissolved in 100 ml of THF and a tenth mole (3.24 g) of methyl alcohol was added. The well-stirred solution was heated to about 60° C. until its infrared spectrum showed complete conversion of the anhydride to the desired PIBSA hemiester.

To one-half of the above reaction mixture, 4.5 g (0.039 mole) of S2Cl2 were added dropwise while stirring at room temperature, under a nitrogen blanket. The reaction mixture was stirred at 25° C. for ten hours and then heated to 120° C. for another 10 hours with nitrogen sparging. The concentrate featured an IR spectrum with strong absorption bands in the 5.6–5.8 micron region, characteristic of lactone and ester carbonyl absorption bands.

EXAMPLE B5

DITHIO-BIS-(POLYISOBUTENYLSUCCINIC ANHYDRIDE)

About 200 g (ca 0.154 moles) of PIBSA having a $M_n$ of 1080 and a Sap. No. of 72 were dissolved in 100 ml of methylene chloride. While stirring at room temperature under a nitrogen blanket, 10.4 g (0.077 moles) of sulfur monochloride were added dropwise for a period of 15 minutes. The reaction mixture was allowed to stir at room temperature overnight.

One-half of the above adduct was heated to 150° C. for approximately 4 hours. Analytical data on the dehydrohalogenated residue showed 2.08 wt. % sulfur and 0.15 wt. % chlorine.

EXAMPLE B-6

ADDUCT OF SCl2 AND SILICA GEL EXTRACTED PIBSA

About 200 g of diluted Ene PIBSA having a Saponification No. of 84 and $M_n$ 776 were dissolved in one liter of heptane. The solution was mixed with 600 g of silica gel and stirred at room temperature for about twelve hours. The heptane layer was decanted, and the silica gel was washed twice with 500 ml aliquots of heptane.

The PIBSA bound silica gel was subsequently extracted with one liter of boiling THF. Rotoevaporation at 80° C. for 2 hours afforded 101 g of a polyisobutylene and oil-free PIBSA residue which featured a Saponification Number of 118 8, a GPC maximum peak of $M_n$ 1227, and a vapor phase osmometry mol. wt. of 1090.

About 10 g of the neat PIBSA (ca. 0.01 mole) were dissolved in 50 ml of THF and stirred at room temperature while 0.8 g (ca 0.0075 mole) of SCl2 were added dropwise. The reaction mixture was stirred at room temperature for twelve hours. Rotoevaporation of the THF solvent gave a residue which featured an IR spectrum with a strong anhydride carbonyl absorption band at 5.65 micros, a gel permeation chromatogram having a maximum peak at 1482 and featuring a molecular weight of 2177 according to vapor phase osmometry (VPO). The analytical data clearly show that the SCl2 bridging of neat PIBSA was virtually quantitative.

The following examples illustrate a novel solid phase synthesis of thio-bis-(acylating agents), wherein the PIBSA is purposely bound, or adsorbed, on a solid phase such as silica gel, and subsequently bridged with a sulfenylating agent such as SCl2. Frequently, the adsorbed sulfur bridged PIBSA product lactonizes directly on the silica gel surface in the presence of water or an alcohol.

EXAMPLE B7

THIO-BIS-(POLYISOBUTYL LACTONE ACID) VIA SULFENYLATION OF SILICA GEL-BOUND PIBSA WITH SCl2

Approximately 100 g of Ene PIBSA of $M_n$ 776 and Sap. No. of 66 were dissolved in one liter of hexane and stirred at room temperature while 400 g of silica gel were added. After stirring the slurry for several hours, the hexane was decanted and silica gel was washed twice with 500 ml of hexane. The hexane fraction was evaporated producing 60 g of material. The silica gel-bound PIBSA was stirred in heptane while 2.1 g (ca. 0.02 mole) of SCl2 were added. The reaction mixture was stirred at room temperature for a few hours and then refluxed in heptane containing small amounts of water for about 12 hours. At the end of the refluxing period, the heptane was decanted and the silica gel was extracted twice with 200 ml portions of boiling THF. The THF solutions afforded a quantitative yield of thio-bis (polyisobutyl lactone acid) as indicated by infrared analysis. The product analyzed for 1.5% S.

EXAMPLE B8

BRIDGING OF SILICA GEL-BOUND CL-PIBSA WITH SCl2

About 100 g of Diels-Alder PIBSA having a $M_n$ of 751 and a saponification number of 80 were dissolved in 500 ml of pentane and mixed with 300 g of silica gel. The mixture was stirred at room temperature for about 12 hours and the pentane phase was decanted. The silica gel was washed twice with 500 ml of pentane and the pentane fraction was evaporated. About 54 g of PIBSA were left on the silica gel. Then, 500 ml of heptane were added and the mixture was well stirred while 3.3 g (ca 0.027 mole, 85% purity) of sulfur dichloride were added dropwise. The mixture was stirred at room temperature for one hour. A gel chromatogram of sulfur-bridged PIBSA sample desorbed from silica gel with THF featured a maximum peak at $M_n$ 606. The GPC of the starting PIBSA exhibited a maximum peak at 465. The reaction mixture containing 2 grams of water, was then refluxed in heptane for 12 hours. Thereafter, the heptane was decanted and the silica gel was extracted with 500 ml of THF twice, giving 22 g of partially lactonized bridged product which featured a GPC with a maximum peak at $M_n$ 550. The silica gel was then extracted twice more with 500 ml of hot THF to yield 15 g of a lactone acid product which featured a gel chromatogram with maximum peak at $M_n$ 580.

C. ESTERIFICATION OF MODEL THIO-BIS-ACYLATING AGENTS

In the following examples, the conventional ester synthesis and template procedures are employed in the design of polyol and polyalkylene glycol esters of model thio-bis-(acylating reagents) comprizing thio-bis-(lactone acids) and adducts of $S_xCl_2$ and olefin diacid derivatives. In the equimolar reaction, the conventional route usually affords mixtures of cyclic and linear ester products, while the template procedure provides mixtures of ester product enriched with 1:1, 2:2 and larger macrocyclic esters.

EXAMPLE C1

BIS-PENTAERYTHRITOL ESTER OF 6,6'-THIO-BIS-(5-NEO-PENTYL-3,5-CARBOLACTONE--HEXANOIC ACID)

A tenth-mole (13.6 g) of pentaerythritol and 0.05 mole of thio-bridged lactone acid (prepared via the addition of $SCl_2$ to diisobutenylsuccinic acid) were mixed in 100 ml of xylene, and heated to reflux. After heating at 180° C. for three hours, the xylene was removed by rotoevaporation, and the reaction mixture dissolved in hot acetone and filtered (2 grams of pentaerythritol collected.) Rotoevaporation of the filtrate gave a concentrate which featured an IR spectrum with hydroxyl, lactone carbonyl and ester carbonyl absorption bands at 2.9, 5.65 and 5.73 microns.

EXAMPLE C2

TRIPENTAERYTHRITOL ESTER OF 6,6''-THIO-BIS-(5-NEO-PENTYL-3,5-CARBOLACTONE-HEXANOIC ACID)

An equimolar mixture of tripentaerythritol 0.05 mole, 18.4 g) and thio-bridged lactone acid (prepared via sulfenylation of diisobutenylsuccinic acid with $SCl_2$) were added to 100 ml of dimethylsulfoxide and heated to 180° C. The resulting solution was stirred at 180°-190° C. for an hour. The IR spectrum of the reaction product was consistent with the expected sulfur-bridged lactone polyol ester.

The preceding Examples show the preparation of said esters with a reactant ratio of 1–2 moles of polyol per mole of thio-bridged lactone acid.

EXAMPLE C3

NEO-PENTYL GLYCOL ESTER OF 6,6'-DITHIO-BIS-(3,5-CARBOLACTONE-1UN-DECANOIC ACID) VIA ALCOHOLYSIS OF THE ADDUCT OF $S_2Cl_2$ AND NOSA

Two-tenths mole (42.0 g) of n-octenylsuccinic anhydride in 100 ml of toluene was treated dropwise with 0.1 mole (13.5 g) of $S_2Cl_2$ at about 25° C. After stirring the reaction mixture for several hours, 0.1 mole (10.4 g) of neopentyl glycol were added portionwise over a 15-minute period with external cooling, and then refluxed for 24 hours. Rotoevaporation at 100° C. for 5 hours gave the product as a residue which featured an IR spectrum dominated by intense ester and lactone carbonyl absorption bands at 5.85 and 5.67 microns.

An ester product could also be realized by $S_2Cl_2$-bridging the hemiester from neopentyl glycol and n-octenylsuccinic anhydride.

EXAMPLE C4

ETHYLENE GLYCOL ESTER OF 6,6'-DITHIO-BIS-(3,5-CARBOLACTONE-UNDECANOIC ACID) VIA ALCOHOLYSIS OF THE $S_2Cl_2$-NOSA ADDUCT

The bridging of n-octenyl succinic anhydride (0.2 mole, 42 g) with $S_2C_2$ (0.1 mole, 13.6 g) was effected by dropwise addition of the sulfur halide to said anhydride in 100 ml xylene at 0° C. Esterification of the resulting bridged anhydride with 0.1 mole (6.2 g) of ethylene glycol afforded a sulfur-bridged lactone ester after refluxing the reactants for several hours.

A lactone ester could also be designed via $S_2Cl_2$-bridging of the hemiester from n-octenylsuccinic anhydride and ethylene glycol after refluxing the mixture in methylene chloride for several hours.

Gel permeation chromatography of the latter ester showed the presence of a substantial peak ($M_n$ of 474 ) consistent with an intramolecular ester of the sulfur-bridged structure.

EXAMPLE C5

2,2-DITHIO-BIS-ETHANOL ESTER OF 6,11-DIPENTYL-3,5:14,12-LACTONE-7,10-DITHIAHEXADECANE-1,16-DIOIC ACID

Bridging of n-octenylsuccinic anhydride (0.1 mole, 21 g) with 1,2-ethane- bis-sulfenyl chloride (0.05 mole) was effected in 100 ml of chloroform at ca 25° C. via the dropwise addition of the sulfenyl chloride to the anhydride After stirring the reaction mixture overnight at ca 25° C., the thio-bridged anhydride was esterified with 0.05 mole (7.7 g) of 2,2'-dithio-bis-ethanol at reflux temperature. The presence of the product lactone ester was confirmed by IR analysis.

EXAMPLE C6

ESTER PRODUCT FROM POLYETHYLENE GLYCOL AND THE ADDUCT OF $S_2Cl_2$ AND n-OCTENYL SUCCINIC ANHYDRIDE (a) Without metal assistance (conventional synthesis) One-tenth mole (55.5 g) of the adduct obtained from the reaction of 0.2 mole of n-octenyl succinic anhydride and 0.1 mole $S_2Cl_2$ was dissolved in 100 ml of xylene and ca 0.1 mole (40 g) of polyethylene glycol - 400 were added. The reaction mixture was heated to the refluxing temperature of the xylene. After 3 hours at about 140° C., an infrared spectrum of the crude mixture showed mainly lactone ester with some unreacted carboxylic acid. The mixture was allowed to reflux overnight to assure complete esterification. The reaction product was washed three times with 100 ml of saturated aqueous $Na_2CO_3$ solution and the xylene layer was dried over $MgSO_4$. Rotoevaporation of the reaction mixture at 100° C. for several hours afforded a residue which featured an infrared spectrum with characteristic absorption bands for ester and lactone functionality.

The GPC scan of the above product showed a peak maximum corresponding to a $M_n$ of 3385.

(b) With metal assistance (template procedure) One-tenth mole (55.5 g) of said adduct of $S_2Cl_2$ and n-octenyl succinic anhydride was dissolved in 200 ml of (tetrahydrofuran) THF and mixed with 19.9 g (0.1 mole) of copper acetate monohydrate. The reaction mixture was heated to reflux and a clear blue solution was obtained. Thereafter ca 0.1 moles (40 g) of polyethylene glycol - 400 was added and the mixture was heated to 80° C. for about 4 hours. During reflux, a solid formed and the blue color of the solution turned dark green. The THF was boiled off and 200 ml of toluene was added and the reaction mixture was again refluxed for two more hours to ensure complete esterification. Filtration produced 8.6 g of a greenish-yellow solid which turned light blue with exposure to air. Analysis showed this solid to be copper chloride. The filtrate was rinsed three times with 100 ml of saturated aqueous $Na_2CO_3$ solution, then dried over $MgSO_4$ and concentrated by rotoevaporation at 100° C. for 4 hours. The infrared analysis of the residue showed absorption bands characteristic of a lactone ester product. GPC analysis indicated a $M_n$ of 1482 for the lactone ester.

In the following Examples thio-bis-(lactone ester) formation was effected via option (2) wherein (i) the potassium carboxylate salt of thio-bis(lactone-acid) was reacted with a dichloride derivative of tetraethylene glycol, (ii) the metal glycolate salt of tetraethylene glycol was interacted with the diacid chloride of thio-bis-(lactone acid) and finally, (iii) the metal carboxylate salt of the hemi-ester from tetraethylene glycol and 2 moles of NOSA was bridged with sulfur dichloride.

EXAMPLE C7

THIO-BIS-(LACTONE ESTER) FORMATION VIA THE POTASSIUM SALT OF THIO-BIS-(LACTONE ACID)

About 24.3 g (ca. 0.05 mole) of 6,6'-thio-bis-(3,5-carbolactone-undecanoic acid) were dissolved in 100 ml of dimethylformamide (DMF) and heated to reflux in the presence of 5.6 g (ca. 0.1 mole) of KOH, until all the KOH dissolved. A clear reddish-brown solution of the dipotassium salt was obtained. Then, 11.6 g (ca 0.05 mole) of 1,11-dichloro-3,6,9-trioxaundecane were added. The reaction mixture was heated to reflux for about 4 hours. At the end of the fourth hour, the potassium chloride that formed was filtered, and the DMF solvent was distilled off at 100° C. under high vacuum. The infrared spectrum of the clear reddish, oily residue featured absorption bands ascribable to the desired lactone ester product. Similar results were obtained when an excess of the dichloride reactant was used.

EXAMPLE C8

THIO-BIS-(LACTONE ESTER) FORMATION VIA THE SODIUM SALT OF TETRAETHYLENE GLYCOL

About 0.1 mole of the diacid chloride of 6,6'-thio-bis-(3,5-carbolactone-undecanoic acid) (prepared via the reaction of thionyl chloride with the lactone acid) was added to a slurry of 0.1 mole sodium glycolate of tetraethylene glycol in 100 ml of xylene (prepared via the reaction of sodium metal and tetraethylene glycol in refluxing xylene) under a nitrogen blanket for a period of one half hour. The reaction mixture was then heated to reflux in xylene for two hours. The sodium chloride by-product was filtered off and the xylene was evaporated with nitrogen sparging. The GPC analysis showed that the residue had a $M_n$ of 904.

The oily residue featured an infrared spectrum with characteristic absorption bands for ester and lactone functionality.

EXAMPLE C9

CHLOROSULFENYLATION OF THE TETRAETHYLENE GLYCOL HEMIESTER OF n-OCTENYL SUCCINIC ANHYDRIDE (a) Without metal assistance The hemiester 0.05 mole (30.7 g) of n-octenyl succinic anhydride and tetraethylene glycol dissolved in 200 ml of THF was chlorosulfenylated via the dropwise addition of 0.05 moles (5.15 g) of $SCl_2$ to the reaction mixture.

An exothermic reaction (with HCl evolution) was observed during the addition. The mixture was stirred overnight at room temperature and then refluxed in THF for 8 hours. An infrared spectrum of the solvent free product showed the presence of lactone ester product. Washing a chloroform solution of the product several times with 100 ml of aliquots of saturated aqueous $Na_2CO_3$ and drying over $MgSO_4$ afforded after rotoevaporation, a lactone ester product analyzing for 4.22 wt. % S. A gel chromatogram of the lactone ester product featured a peak maximum of $M_n \approx 2097$.

(b) With metal assistance and $SCl_2$

One-tenth mole (60.4 g) of the hemiester of tetraethylene glycol and n-octenylsuccinic acid was dissolved in 200 ml of THF and heated with 0.01 mole (19.9 g) of copper diacetate and a clear blue solution was obtained. Thereafter the THF solution was allowed to cool down to room temperature and 0.05 mole (5.15 g) of $SCl_2$ were added dropwise. An exothermic reaction took pace and some solid precipitated out after a few minutes. After refluxing 8 hours, the reaction mixture was cooled and filtered about 9 g of $CuCl_{12}$ were obtained). The solvent was evaporated and the residue was dissolved in 200 ml chloroform washed several times with aqueous $Na_2CO_3$, and dried. Infrared analysis showed that the residue featured lactone and ester functionality. The product analyzed for 5.03 wt. % S and exhibited a $M_n$ of 1227 based on the GPC peak maximum.

(c) With metal assistance and $S_2Cl_2$

The same procedure as above was repeated using $S_2Cl_2$. A lactone ester product was obtained which contained 10.54 wt. % S and featured a $M_n$ of 600 based on the GPC peak maximum.

EXAMPLE C10

BIS-PENTAERYTHRITOL ESTER OF 6,6'-DITHIO-BIS-(3,5-CARBOLACTONE-1HENEICOSANOIC ACID)

The adduct of $S_1Cl_2$ and octadecenylsuccinic anhydride (0.05 mole, 40.2 g) was esterified with 0.1 mole (13.6 g) of pentaerythritol in refluxing xylene (100 ml). HCl evolution was observed. Partial distillation of the xylene solvent raised the reaction temperature to 180° C. After maintaining reaction at 180° C. for several hours, the xylene was removed via rotoevaporation. Dissolution of the residue in hot acetone clouded with ether afforded upon cooling, a solid product which featured an IR spectrum with strong hydroxyl, lactone carbonyl, and ester carbonyl absorption bands at 3.05, 5.65 and 5.75 microns, respectively.

n the following Examples, the thio-bis-(lactone acid) derived from OSA was esterified via the (a) conventional method and (b) the template method wherein the metal template reagent e.g. tetrabutyl titanate, is added in catalytic amounts to a mixture of polyol and thio-bis-(acylating agent).

EXAMPLE C11

BIS(2,2,6,6-TETRAMETHYLOL-1-CYCLOHEXANOL) ESTER OF 6,6-THIO-BIS-(3,5-CARBOLACTONE-HENEICOSANOIC ACID)

About 38.3 g (ca 0.05 mole) of 6,6'-thio-bis-(3,5-carbolactone-1.heneicosanoic acid) were dissolved in 100 ml of xylene and mixed with 22 g of TMC (0.1 mole) and 0.1 g of p-toluenesulfonic acid. The reaction mixture was refluxed for about 1½ hour until about 8 cc of water were collected. The mixture was heated another hour to assure complete reaction. The xylene was removed by rotoevaporation, and the residue was dissolved in pentane and filtered. Evaporation of the pentane afforded a quantitative yield of a white solid which featured an infrared spectrum consistent with the title lactone ester. The hydroxyl number for the lactone ester product was found to be 99.2. GPC analysis shows a $M_N$ of 1783.

EXAMPLE C12

2,2,6,6-TETRAMETHYLOL-1-CYCLOHEXANOL ESTER OF 6,6'-THIO-BIS-(3,5-CARBOLACTONE-1-HENEICOSANOIC ACID)

About 38.3 g (ca 0.05 mole) of 6,6'-thio-bis-(3,5-carbolactone-1-heneicosanoic acid) dissolved in 100 ml of xylene were mixed with 11 g (0.05 mole) of 2,2,6,6-tetramethylol-1-cyclohexanol (TMC) and 0.1 g of p-toluene sulfonic acid. The mixture was heated to about 140°-145° C. to azeotrope the water of reaction. At the end of the third hour, the reaction was completed as indicated by the cessation of water and infrared analysis. The xylene was stripped off with nitrogen and the residue was diluted with about 1 liter of a 50/50 ether-acetone mixture. A white solid precipitated upon cooling; filtration gave 22 g of the desired lactone ester product. Further cooling gave an additional 17 g of solid, which was identical to the first crop as determined by infrared analysis. The product featured a hydroxyl number of 44.9 and a gel chromatogram with $M_n \approx 3555$.

EXAMPLE C13

TETRABUTYL TITANATE CATALYZED ESTERIFICATION OF 6,6'-THIO-BIS(3,5-CARBOLACTONE-1-HENEICOSANOIC ACID) WITH 2,2,6,6-TETRAMETHYLOL-1-CYCLOHEXANOL (TMC)

About 38.3 g (ca 0.05 mole) of thio-bis-(lactone acid) derived from OSA were dissolved in 100 ml of xylene and mixed with 1 g (ca 0.05 mole) of TMC and 5 g of tetrabutyl titanate. The reaction mixture was refluxed to remove the water of reaction completely. After the third hour, the hazy solution was filtered, and the clear filtrate was rotoevaporated under high vacuum at 100° C. for about six hours. A waxy solid material was obtained which featured an IR spectrum characteristic of the desired lactone ester. The product analyzed for 3.93 wt. % sulfur, and featured a GPC with $M_n$ of 1353, a value which is consistent with the presence of substantial amounts of macrocyclic and macrocyclic-like products.

D. ESTERIFICATION OF MACRO THIO-BIS-(ACYLATING AGENTS) WITH POLYOLS The following Examples illustrate the esterification of Ene and Diels-Alder type thio-bis-(polyisobutyl lactone acid), thio-bis-(polybutene diacid anhydride) and adducts of $S_xCl_2$ and PIBSA with 1-2 moles of polyols such as pentaerythrithol and tripentaerythritol.

EXAMPLE D1

BIS-PENTAERYTHRITOL ESTER OF THIO-BIS-(POLYISOBUTYL LACTONE ACID)

Approximately 0.01 mole (26.3g) of the thio-bis-(polyisobutyl lactone acid) prepared as described in Example B1 and 0.02 mole (2.8g) of pentaerythritol were mixed and heated to 200° C. for 2 hours. The product was diluted with an equal weight of Solvent 150 Neutral oil and filtered. Infrared analysis of the filtrate featured characteristic absorption bands at 2.9-3.0 (hydroxyl) and a broad band in the 5.65-5.8 micron region (lactone ester) The hydroxyl number for the product solution (50 wt. %) was found to be 83 and showed a GPC peak maximum at $M_n \approx 7000$.

EXAMPLE D2

PENTAERYTHRITOL ESTER OF THIO-BIS-(POLYISOBUTYL LACTONE ACID)

Approximately 0.01 mole (26.3g) of thio-bis-(polybutyl lactone acid) prepared as described in Example B2 and dissolved in 26.3g of Solvent 150 Neutral oil and 0.01 mole (1.36g) of pentaerythritol were mixed and heated to about 130° C. The temperature was raised to 200° C. and maintained there for 2 hours. Infrared analysis of the filtered solution having about 50 wt. % a.i. showed the presence of hydroxyl, lactone and ester functionality and analyzed for 0.39% sulfur. The hydroxyl number for the product solution was found to be 48.5.

EXAMPLE D3

BIS-PENTAERYTHRITOL ESTER OF DITHIO-BIS-(POLYISOBUTYL LACTONE ACID)

80 g (ca. 0.03 moles) of a dithio-bis-(polyisobutyl lactone acid) product prepared as described in Example B3 was heated to 190° C. While stirring under nitrogen blanket, 9.8 g (0.072 moles) of pentaerythritol were added and the stirred reaction mixture was heated to 220° C. for three hours with nitrogen sparging. At the end of the third hour, an equal amount of Solvent 150 Neutral oil was added to the residue to provide a 50 wt. % a.i. solution. This solution was diluted with 200 ml of hexane and filtered, and then rotoevaporated at 100° C. for 3 hours. The resulting product solution disclosed an infrared spectrum with prominent carbonyl absorption bands ascribable to the desired lactone polyol ester product which featured a hydroxyl number of 90.8 and a GPC with peak maximum at $M_n \approx 4100$ and 8100.

EXAMPLE D4

BIS-PENTA(RYTHRITOL ESTER OF THIO-BIS-(POLYALKENE DIACID ANHYDRIDE)

50 g (ca 0.02 moles) of the adduct prepared according to the first paragraph of Example B3 was heated to 190° C. for 2 hours while stirring under nitrogen 6.5 g (0.048 mole) of pentaerythritol were added and the stirred reaction mixture was heated to 220° C. for 3 hours with nitrogen sparging. At the end of the third hour, an equal volume of Solvent 150 Neutral mineral oil was added to the residue to provide a 50 wt. % product solution This solution was filtered through a filter cake of Celite 503. The resulting product solution exhibited an infrared spectrum with prominent carbonyl absorption bands consistent with an ester product, featured a hydroxyl number of 106.1, and analyzed for 1.29 wt. % sulfur and 0.18 wt. % chlorine.

EXAMPLE D5

PENTAERYTHRITOL (PE) ESTER OF THIO-BIS-(POLYISOBUTYL LACTONE ACID)

Approximately 200 g (0.1 mole) of a 50 wt. % active ingredient of PIBSA having a Sap. No. of 84 and a $M_n$ of 776 in S150 neutral mineral oil obtained via the Ene process were dissolved in 200 ml of $CH_2Cl_2$ and stirred at room temperature under a nitrogen atmosphere. The solution was chlorosulfenylated via the dropwise addition of 7.5 g (0.075 mole) of $SCl_2$ for a period of ten minutes while at room temperature. Hydrogen chloride evolution was observed during this process accompanied by an exothermic reaction. The mixture was stirred at room temperature overnight; then 13.6 (0.1 mole) of PE and 0.5 g of concentrated sulfuric acid were added. The slurry was heated gradually to distill off the solvent and then to 210°-215° C. for 3 hours while nitrogen sparging At the end of the third hour the product was filtered and collected. An infrared spectrum of the solution product featured prominent carbonyl absorption band ascribable to the desired lactone polyol ester products

EXAMPLE D6

BIS-2,2,6,6-TETRAMETHYLOL-1-CYCLOHEXANOL ESTER OF THIO-BIS-(POLYISOBUCTYL-LACTONE ACID)

Approximately 0.025 mole of the adduct of PIBSA having a Sap. No. of 84 and a $M_n$ of 776 and $SCl_2$, prepared via the room temp. addition of $SCl_2$ to a 50% a.i. PIBSA in Solvent 150 neutral mineral oil, was mixed at room temperature with 11.0g (0.05 mole) of 2,2,6,6-tetramethylolcyclohexanol. The reaction mixture was gradually heated to 210°-215° C. for a period of 3 hours while stirring and nitrogen sparging. The lactone formation was monitored by infrared spectroscopy At the end of the third hour (lactone ester carbonyl absorptions in IR reached maximum), the solution product was filtered and collected. The product showed prominent absorption bands characteristic of lactone and ester functionality.

EXAMPLE D7

TRIPENTAERYTHRITOL ESTER OF DITHIO-BIS-(POLYISOBUTYL LACTONE ACID)

Approximately 153 g ( 0.15 mole) of polyisobutenyl succinic anhydride ($M_n$) of 757 having a Sap. No. of 112 and prepared via the (ne reaction of PIB and maleic anhydride were dissolved in 200 ml of THF and stirred at room temperature under a nitrogen blanket. Thereafter 10.7 g (.077 ) of $S_2Cl_2$ were added dropwise for a period of 15 minutes. The mixture was stirred overnight at room temperature.

Approximately 56 g of the above solution containing about 0.01 mole of the adduct was mixed with 3.7 g (0.01 mole) of tripentaerithritol and gradually heated to 200°-210° C. for 3 hours while nitrogen sparging.

At the end of the third hour the reaction product was mixed with an equal weight of Solvent 150 neutral mineral oil. The filtered product featured and infrared spectrum with absorption bands at 2.9–3.0 microns, and a broad band at 5.75–5.85 microns characteristic of hydroxyl, lactone and ester functionality.

EXAMPLE D8

REACTION PRODUCT OF THE ADDUCT OF $S_2Cl_2$ AND PIBSA WITH TRIPENTAERYTHRITOL 210 g (ca. 0.15 mole) of PIBSA, $M_n$ of 1050 and a Sap. No. of 78.9), were heated to 100° C. while stirring under nitrogen Then, 13.6 g (0.1 mole) of $S_2Cl_2$ were added dropwise over a period of 15 minutes. Upon completion of the addition, the reaction mixture was nitrogen sparged for one-half hour at 100° C. Then 70 g (ca. 0.025 mole) of the dithio-bis-(polyisobutylsuccinic anhydride) prepared as above were mixed with 9.3 g (0.025 mole) of tripentaerythritol and gradually heated to 215° C. The reaction mixture was kept at 215° C. for 3 hours with nitrogen sparging. At the end of the third hour, an equal weight of Solvent 150 neutral mineral oil was added and the oil solution was filtered. The filtrate featured an IR spectrum characteristic of the polyol ester compounds and analyzed for 0.72 wt. % sulfur.

EXAMPLE D9

PENTAERYTHRITOL ESTER OF AN $SCl_2$-PIBSA ADDUCT 70 g (ca 0.05 mole) of PIBSA $M_n$ of 1080 and a Sap. No. of 78.9, were reacted successively with 4.0 g (0.04 mole) of $SCl_2$ and 8.1g (0.06 mole of pentaerythritol, according to Example D8. The product solution featured an infrared spectrum with hydroxyl absorption at 2.9 microns and intense ester carbonyl absorption in the 5.75–5.85 micron region. The ester product analyzed for 0.54% sulfur, 0.3% Cl and showed a hydroxyl number of 46.9.

EXAMPLE D10

BIS-PENTAERYTHRITOL ESTER OF A S₂Cl₂-PIBSA ADDUCT

Seventy grams (ca 0.05 mole) of the PIBSA used in Ex. D9 was sulfenylated with 4.4 g (0.33 mole) of $S_2Cl_2$ at 25° C. and then esterified with 8.2 g (0.06 mole) of pentaerythritol at 210° C. for 3 hours. The infrared spectrum of the final product solution showed absorption bands similar to those in Example D9.

PENTAERYTHRITOL ESTER OF AN SCl₂PIBSA ADDUCT FORMED AT 100° C.

Approximately 100 g of polyisobutenyl succinic anhydride of $M_n$ 776 by GPC and having a saponification number of 84 were charged into a reaction flask and heated to 100° C. Thereafter 13.6 g (0.1 mole) of $S_2Cl_2$ were added while stirring at 100° C. under a nitrogen atmosphere, for a period of one half hour. When the addition was completed the reaction mixture was kept at 100° C. for one half hour and then nitrogen sparged for another half hour. The adduct analyzed for 1.25 wt. % chlorine While keeping the reaction temperature at 100° C., 16.3 g (0.12 mole) of pentaerythritol were added and the reaction temperature was gradually raised to 210°–215° C. for a period of 3 hours. At the end of the third hour an equal amount of Solvent 150 neutral mineral oil was added and the product was filtered. An analysis of the product solution showed 0.36 wt. % Cl and 2.05 wt. % S and a hydroxyl number of 66.1. An infrared spectrum of the product featured several broad absorption bands consistent with polyol ester product.

EXAMPLE D12

BIS-PENTAERYTHRITOL ESTER OF THE S₂Cl₂-PPSA ADDUCT

Approximately 122 g (ca 0.1 mole) of a polypropenylsuccinic anhydride (PPSA), (prepared by the Ene process using polypropylene and maleic anhydride), having a $M_n$ of 623 by GPC (peak maximum at $M_n$ 938) and a saponification number of 92, were dissolved in 200 ml of THF and stirred at room temperature under a nitrogen blanket. Then, the above product was chlorosulfenylated via the dropwise addition of 6.8 g (0.05 mole) of $S_2Cl_2$ at room temperatures. The reaction mixture was stirred at room temperature for 24 hours and then rotoevaporated under high vacuum 90° C. for two hours.

About 60 g (ca 0.025 mole) of the adduct prepared according to the above paragraph were mixed with 66 g of mineral oil S150 neutral and 8.1 g (0.06 mole) of PE and gradually heated to 215° C. The reaction temperature was kept at 215° C. for 3 hours with nitrogen sparging. After the third hour, the product was filtered and collected. The resulting product solution featured an infrared spectrum with prominent ester carbonyl absorption bands consistent with the desired product.

EXAMPLE D13

PENTAERYTHRITOL ESTER OF A DEHYDROCHLORINATED SCl₂-Cl-PIBSA ADDUCT (DIELS-ALDER)

Approximately 150 g of PIBSA of $M_n$ 1044, having a saponfication number of 103, were heated to 100° C. While stirring under a nitrogen atmosphere, 15.5 g of $SCl_2$ were added dropwise for a period of 10 minutes, and then sparged with nitrogen for half hour. At this point, 80 g of Solvent 150 neutral mineral oil were added and the reaction temperature was raised to 200° C.; thereafter 20.6 g of PE were added and the mixture was heated at 215° C. for 3 hours under a nitrogen blanket. At the end of the third hour, 90 g of S150 neutral were added and the product was sparged with nitrogen for another hour. The filtered product analyzed for 0.46% sulfur.

EXAMPLE D14

PENTAERYTHRITOL ESTER OF AN SCl₂-Cl-PIBSA ADDUCT (DIELS-ALDER)

Approximately 2000 g of a PIBSA of $M_n$ of 1044, having a saponification number of 103 were dissolved in 4 liters of heptane and filtered through a filter cake of celite. The heptane was distilled off until constant weight and the residue analyzed for a saponification number of 90.2.

About 1500 g (ca 1.21 mole) based on a Sap. No. of 90.2 were heated to 100° C., and 103 g (1 mole) of $SCl_2$ were added dropwise over a period of one half hour. The stirred solution was kept at 100° C. for one half hour and then sparged with nitrogen for another half hour. At this point, 450 g of solvent 150 neutral mineral oil and 190 g (1.39 mole) of PE were added and the reaction mixture was gradually heated to 215° C. for 3 hours with nitrogen sparging. At the end of the third hour, 1227 g of solvent 150 neutral were added and the product solution was sparged with nitrogen for another hour.

The filtered reaction mixture was analyzed for 0.45 wt. % S, and featured a hydroxyl number of 37.0.

EXAMPLE D15

PENTAERYTHRITOL ESTER OF AN S₂Cl₂-Cl-PIBSA ADDUCT (DIELS-ALDER)

One hundred fifty grams (ca. 0.14 mole) of polyisobutenylsuccinic anhydride ($M_n$ of 1055 and Sap. No. of ca 103) were successively reacted with 13.5 g (0.1 mole) of sulfur monochloride and 22.5 g (0.16 mole) of pentaerythritol as described in Example D13. The infrared spectrum of the residue featured broad bands at (2.9–3.0) microns and 5.75–5.85 microns. After dissolution in an equal weight of S150N mineral oil, the ester product analyzed for 0.61 wt. % sulfur.

EXAMPLE D16

PENTAERYTHRITOL ESTER OF AN SCl₁₂-Cl-PIBSA ADDUCT (DIELS-ALDER)

The procedure of Example D13 was followed except that the PIBSA (150 g) had a $M_n$ of 771 and a Sap. No. of 112, the amount of $S_2Cl_2$ was 20.3 g and the amount of pentaerythritol was 20.6 g (0.15 mole). The reaction product was dissolved in an equal weight of Solvent 150N mineral oil and analyzed for 0.61 wt. % sulfur.

EXAMPLE D17

PENTAERYTHRITOL ESTER OF AN S₂Cl₂-Cl-PIBSA ADDUCT (DIELS-ALDER)

The procedure of Example D13 was followed except that 20.3 g of $S_2Cl_2$ and 20.6 g (0.15 mole) of pentaerythritol were used and one-half, i.e. about 80 g of S150N mineral oil, was added prior to the addition of pentaerythritol and the balance, i.e. 80 g, of S150N mineral oil was added after esterification. The filtered reaction product analyzed for 0.78 wt. % sulfur.

EXAMPLE D18

BIS-PENTAERYTHRITOL ESTER OF A DEHYDROCHLORINATED S₂Cl₂-PIBSA ADDUCT 26.5 g of the dithio-bis-(polyisobutenylsuccinic anhydride) product prepared in Example B5 was mixed with 2.9 g (ca 0.022 moles) of pentaerythritol and heated to 200°–220° C. for 3 hours with stirring and nitrogen sparging. At the end of the third hour, an equal weight of Solvent 150 neutral oil was added to the residue to provide a 50 wt. % a.i. solution. The reaction mixture was filtered through a cake of Celite. The resulting product solution disclosed an infrared spectrum with broad hydroxyl and carbonyl absorption bands consistent with the bis-(pentaerythritol ester) of dithio-bis-(polybutenylsuccinic acid).

EXAMPLE D19

BIS-PENTAERYTHRITOL ESTER OF DEHYDROCHLORINATED S₂Cl₂-Cl-PIBSA ADDUCT (DIELS-ALDER)

About 312 g (ca 0.28 mole) of PIBSA having a $M_n$ of 1044 and a saponification number of 103 was charged into a reaction flask and dissolved in 300 ml of methylene chloride while stirring under a nitrogen at 25° C. Thereafter 18.9 g (ca 0.14 mole) of $S_2Cl_2$ were added dropwise for a period of one half hour. The stirred reaction mixture was allowed to stand at room temperature for about 20 hours.

Approximately one third (ca 0.037 mole) of the above mixture was heated to distill off the solvent and then kept at 160° C. for one hour. Hydrogen chloride evolution was observed during this period. A sample of this mixture analyzed for 0.50 wt. % Cl and 2.31 wt. % S. At this point, 12.4 g (0.091 mole) of pentaerythritol were added and the mixture was gradually heated to 210°–215° C. for three hours while nitrogen sparging. The resulting product was dissolved in hexane, filtered, and rotoevaporated at 100° C. under high vacuum until constant weight. The residue was dissolved in an equal weight of solvent 150 neutral mineral oil. The infrared spectrum of said product solution was consistent with a polyol ester product.

EXAMPLE D20

BORATED PENTAERYTHRITOL ESTER OF DITHIO-BIS-(POLYISOBUTYL LACTONE ACID)

50 g of the product solution of Example D3 and 1.1 g of boric acid were heated at 120° C. for 2 hours and then filtered hot. The resulting borated product solution contained 0.38 wt. % boron and 1.69 wt. % sulfur. The product solution of Example D3 prior to the above boration step featured an infrared spectrum with a prominent hydroxyl absorption band at 2.9 microns. This band was substantially reduced in the infrared spectrum of the borated product solution of Example 20.

Boron compounds useful in the boration reaction of the oil-soluble polyol esters of thio-bis-(hydrocarbyl substituted acid materials) of the invention include boron oxide, boron oxide hydrate, boron acids such as boronic acid (e.g., alkyl-B(OH)₂ or aryl-B(OH)₂) and boric acids, preferably H₃BO₃, and esters of such boron acids.

Specific examples of boronic acids include methyl boronic acid, phenylboronic acid, cyclohexyl boronic acid, p-heptylphenyl boronic acid and dodecyl boronic acid.

The boric acid esters include mono-, di- and tri-substituted organic esters of boric acid with alcohols or phenols such as e.g., butanol, octanol, cyclohexanol, cyclopentanol, ethylene glycol, 1,3-butanediol, 2,4-hexaneidol, polyisobutene substituted phenols. Lower alcohols, 1,2-glycols, and 1,3-glycols, i.e., those having less than about 8 carbon atoms are especially useful for preparing the boric acid esters for the purpose of this invention. Methods for preparing the esters of boron acid are known and disclosed in the art (such as "Chemical Reviews" pages 959–1064, volume 56).

The general process of forming the oil-soluble borated, polyol esters of thio-bis-(hydrocarbyl substituted acid materials) of the invention by reacting the thio-bis-(lactone polyol ester) with the boron containing compound is usually carried out by heating a mixture of the reactants at a temperature above about 60° C., preferably within the range from about 80° C. to about 200° C. However, when boric acid or oxide is employed, the process is carried out at a temperature (such as 100° C. to 180° C.) preferably at about 140° C. The use of a solvent such as benzene, toluene, naphtha, mineral oil, xylene, n-hexane, or the like is often desirable in the above process to facilitate the control of the reaction temperature and removal of water; mineral oil is preferred to facilitate the products use as a lubricating oil additive.

The oil-soluble thio-bis-(lactone polyol ester) reacts readily with the boron compounds, e.g., boric acid at these mildly elevated temperatures to form the boron esters of the invention. If water of reaction is formed in the reaction as with the preferred boric acid, it is necessary to remove all or a part of it from the reaction mixture by separating it overhead either by blowing with an inert gas such as nitrogen or by simple azeotropic distillation.

Boration of the materials should provide from about 0.1 to 2.0 wt. %, preferably 0.2 to 1.0 wt. %, boron based on the weight of said material

EXAMPLE D21

PENTAERYTHRITOL ESTER OF PIBSA

About 0.1 mole (200 g of a 51 wt. % solution in S150N oil) of PIBSA having a Sap. No. of 84 and $M_n$ of 776 and 13.6 g (0.1 mole) of pentaerythritol were mixed and heated to 200° C. The reaction mixture was stirred at 200° C. for about 3 hours and then filtered. The filtrate (50% a.i.) featured an infrared spectrum with a strong ester carbonyl absorption band at 5.8 microns and analyzed for 5.04% oxygen. The hydroxyl number for the ester product in solution (50 wt. % a.i.) was determined to be 57.4. GPC analysis revealed that the peak maximum for this type of commercial dispersant was about 25,000.

EXAMPLE D22

SLUDGE INHIBITION BENCH (SIB) TEST

The products of the above examples were subjected to a Sludge Inhibition Bench (SIB) Test which has been found after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 100° F. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersants. A quantity of such used oil was acquired by draining and refilling the taxicab crankcase at 1,000–2,000 mile intervals.

The Sludge Inhibition Bench Test is conducted in the following manner. The aforesaid used crankcase, which is milky brown in color, is freed of sludge by centrifuging for ½ hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-insoluble deposits of sludge. The sludge inhibiting properties of the additives being tested are determined by adding to portions of the supernatant used oil, a small amount, such as 0.5 wt. %, on an active ingredient basis, of the particular additive being tested. Ten grams of each blend being tested is placed in a stainless steel centrifuge tube and is heated at 280° F. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 15 ml of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

Using the above-described test, the dispersant activity of the additive compounds according to the present invention were compared with the pentaerythritol ester of PIBSA (product of Example D21) and a commercially available dispersant (Lz 936) sold by the Lubrizol Corporation of and is believed to be a 60 wt. % mineral oil solution of a ca. equimolar reaction product of PIBSA and pentaerythritol with $M_n$ 25,000 by GPC. The test results are given in Table I.

TABLE I

| SLUDGE DISPERSANCY TEST RESULTS | | |
|---|---|---|
| Test Sample | Additive of Example | Mg Sludge/10 g Oil at 0.5 wt. % |
| I - 1 | D3 | 1.2 |
| - 2 | D21 | 7.4 |
| - 3 | D19 | 3.2 |
| - 4 | D15 | 2.04 |
| - 5 | D16 | 3.6 |
| - 6 | D17 | 2.1 |

TABLE I-continued

| SLUDGE DISPERSANCY TEST RESULTS | | |
|---|---|---|
| Test Sample | Additive of Example | Mg Sludge/10 g Oil at 0.5 wt. % |
| - 7 | D18 | 3.2 |
| - 8 | D4 | 2.4 |
| - 9 | Lz 936 | 10.2, 6.4 |
| - 10 | Blank | 10.0 |

The results set forth in Table I show that the sulfur-bridged polyol ester dispersants according to the present invention are more effective sludge dispersants than the commercial type pentaerythritol esters of PIBSA, i.e. Example D21 and Lz 936 (sold commercially by Lubrizol Corporation as a sludge dispersant for lubricating oils).

EXAMPLE D23

EVALUATION OF PRODUCTS IN VARNISH INHIBITION BENCH (VIB) TEST

Each test sample consisted of 10 grams of lubricating oil containing 0.07 of a gram of the additive concentrate (50% active) which results in a total of 0.35 wt. % additive present in the test sample. The test oil to which the additive is admixed was 9.93 g rams of a commercial lubricating oil obtained from a taxi after 2,000 miles of driving with said lubricating oil. Each ten gram sample was heat soaked overnight at about 140° C. and thereafter centrifuged to remove the sludge. The supernatant fluid of each sample was subjected to heat cycling from about 150° C. to room temperature over a period of 3.5 hours at a frequency of about 2 cycles per minute. During the heating phase, the gas containing a mixture of about 0.7 volume percent $SO_2$, 1.4 volume percent NO and balance air was bubbled through the test samples and during the cooling phase water vapor was bubbled through the test samples. At the end of the test period, which testing cycle can be repeated as necessary to determine the inhibiting effect of any additive, the wall surfaces cf the test flasks in which the samples were contained are visually evaluated. Flasks in which the samples were contained are visually evaluated as to the varnish inhibition. The amount of varnish imposed on the walls is rated at values of from 1 to 7 with the higher number being the greater amount of varnish It has been found that this test correlates with the varnish results obtained as a consequence of carrying out an MS-VC engine test. The results of the VIB testing of candidate and commercial dispersants are recorded in table II below:

TABLE II

| 0.5 WEIGHT PERCENT OF ADDITIVE ADDED TO TEST OIL | | |
|---|---|---|
| Test Sample | Additive of Example | VIB Rating |
| II - 1 | D3 | 4 |
| - 2 | D21 | 5-6 |
| - 3 | D19 | 2 |
| - 4 | D15 | 3 |
| - 5 | D18 | 3 |
| - 6 | D17 | 3 |
| - 7 | D4 | 4 |
| - 8 | D20 | 4 |
| - 9 | Lz 936 | 4 |
| - 10 | Blank | 11 |

The data in Table II illustrate the outstanding varnish-inhibition activity of the additive compounds (including a borated derivative - see Test Sample II-8) according to the present invention when compared with commercial-type Pentaerythritol esters of PIBSA, i.e. Test Samples II-2 and -9, the latter being sold commercially as a sludge dispersant for lubricating oils by the Lubrizol Corporation.

EXAMPLE D24

The utility of the inventive additives was also measured by subjecting the product of Example D8 to a standard engine test of a blended formulation containing this additive A 15W/50 SAE crankcase oil formulation was made up using 12.5 wt. % of the oil concentrate of Example D8, 2 volume % of an ashless dispersant additive, 1.1 volume % of an overbased magnesium sulfonate, 0.8 volume % of overbased calcium phenate, 0.5 volume % of an antioxidant, and 1.43 volume % of a zinc dialkyldithiophosphate and a mineral lubricating oil blend of base stocks. The above formulation was tested in the Sequence V-C Engine Test, which is described in "Multicylinder Test Sequences for Evaluating Automotive Engine Oils", ASTM Special Technical Publication 315F, page 133ff (1973). The V-C test evaluates the ability of a formulated oil to keep sludge in suspension and prevent the deposition of varnish deposits on pistons, valves, and other engine parts. The MS-VC test results for Example are illustrated in Table III.

TABLE III

| | MS-VC Test Results | | |
|---|---|---|---|
| | Sludge | Piston Skirt Varnish | Total Varnish |
| Oil with Product of Ex. D8 | 9.3 | 8.0 | 7.9 |
| Passing Criteria for Test | 8.5 | 7.9 | 8.0 |

In the above tests, the ratings are on a scale of 0 to 10, with 0 being an excessive amount of sludge and varnish while 10 being a completely clean engine. The formulated oil containing the additive of the invention (Example D8) passed.

EXAMPLE D25

Seven of the sulfur-bridged polyol ester products of the present invention and two commercial polyol ester dispersant additives diluted in mineral oil were evaluated by thermo gravimetric analysis (TGA) for evidence of thermal stability under oxidative conditions provided by air flow across each sample heated linearly from about 50° C. to 450° C. at a rate of 6°/min. Each sample of 200 mg in a stainless steel planchette was continuously weighted and recorded as the temperature was programmed upwardly at a linear-rate to provide a record of sample weight versus temperature. The results are found in Table IV.

TABLE IV

| Test Sample No. | Product Additive Tested | Temperature at which the indicated percentage weight loss occurred | | | |
|---|---|---|---|---|---|
| | | 10 Wt. % °C. | 50 Wt. % °C. | 70 Wt. % °C. | 90 Wt. % °C. |
| 1 | Solvent 150N Mineral Oil | 230 | 283 | 295 | 310 |
| 2 | Lz 936* | 220 | 317 | 375 | 417 |
| 3 | Ex. D21 | 245 | 315 | 365 | 410 |
| 4 | Ex. D19 | 265 | 360 | 415 | 450 |
| 5 | Ex. D4 | 280 | 387 | 420 | 450 |
| 6 | Ex. D3 | 270 | 375 | 410 | 437 |
| 7 | Ex. D13 | 265 | 345 | 400 | 442 |
| 8 | Ex. D20 | 270 | 380 | 413 | 430 |
| 9 | Ex. D7 | 263 | 350 | 413 | 452 |
| 10 | Ex. D10 | 265 | 350 | 400 | 437 |

*Lubrizol Lz 936 is a commercial dispersant for lubricant oils sold by Lubrizol Corp., Ohio.

The TGA data shown in Table IV reveal that the compositions of the present invention are significantly more stable towards heat and oxidation than the reference commercial PIBSA polyol ester dispersants, Lz 936 and Ex. D21. In addition, the TGA data show that the thio bis-(polyol esters) of the present invention tends to stabilize the base oil, e.g. S-150N base stock oil, towards thermal oxidative degradation. Thus, the novel structural features built into the present dispersants endow these additives with enhanced thermal stability as well as the ability to inhibit oxidation of the base stock oil. It is believed that these inhibitor properties can be related in part to the presence of sulfide functionality in the additive molecules of the present invention.

What is claimed is:

1. Thio-bis-(polyisobutyl lactone acid pentaerythritol ester).

2. Thio-bis-(polyisobutyl lactone acid bispentaerythritol ester).

3. Dithio-bis-(polyisobutyl lactone acid pentaerythritol ester).

4. Dithio-bis-(polyisobutyl lactone acid bispentaerythritol ester).

5. Thio-bis-(polyisobutyl lactone acid tripentaerythritol ester).

* * * * *